(12) United States Patent
Eastham et al.

(10) Patent No.: US 7,767,864 B2
(45) Date of Patent: Aug. 3, 2010

(54) PROCESS FOR THE HYDROFORMYLATION OF ETHYLENICALLY UNSATURATED COMPOUNDS

(75) Inventors: Graham Eastham, Redcar (GB); David Cole-Hamilton, Fife (GB); Christina Jimenez, Fife (GB)

(73) Assignee: Lucite International UK Limited, Hampshire (GB)

( * ) Notice: Subject to any disclaimer, the term of this patent is extended or adjusted under 35 U.S.C. 154(b) by 0 days.

(21) Appl. No.: 10/561,912

(22) PCT Filed: Jul. 1, 2004

(86) PCT No.: PCT/GB2004/002859

§ 371 (c)(1),
(2), (4) Date: Mar. 23, 2007

(87) PCT Pub. No.: WO2005/003070

PCT Pub. Date: Jan. 13, 2005

(65) Prior Publication Data

US 2008/0051475 A1 Feb. 28, 2008

(30) Foreign Application Priority Data

Jul. 3, 2003 (GB) .................................. 0315536
Jul. 24, 2003 (GB) .................................. 0317242

(51) Int. Cl.
*C07C 45/50* (2006.01)
*B01J 31/00* (2006.01)
*B01J 23/00* (2006.01)

(52) U.S. Cl. .................. 568/454; 502/155; 502/325
(58) Field of Classification Search .............. 568/454; 502/155, 325
See application file for complete search history.

(56) References Cited

U.S. PATENT DOCUMENTS

| 4,377,708 | A | 3/1983 | Morris |
| 4,500,727 | A | 2/1985 | Kitamura et al. |
| 4,504,684 | A | 3/1985 | Fox et al. |
| 4,517,061 | A | 5/1985 | Fauvarque et al. |
| 4,786,443 | A | 11/1988 | Drent et al. |
| 4,900,413 | A | 2/1990 | Tanaka et al. |
| 4,960,926 | A | 10/1990 | Drent |
| 4,960,949 | A | 10/1990 | Devon et al. |
| 5,028,576 | A | 7/1991 | Drent et al. |
| 5,099,062 | A | 3/1992 | Drent et al. |
| 5,103,043 | A | 4/1992 | Drent et al. |
| 5,149,868 | A | 9/1992 | Drent |
| 5,158,921 | A | 10/1992 | Drent et al. |
| 5,166,116 | A | 11/1992 | Drent et al. |
| 5,177,253 | A | 1/1993 | Drent et al. |
| 5,179,225 | A | 1/1993 | Drent et al. |
| 5,189,003 | A | 2/1993 | Klusener et al. |
| 5,210,280 | A | 5/1993 | Drent |
| 5,245,098 | A | 9/1993 | Hamilton et al. |
| 5,246,558 | A | 9/1993 | Chevigne et al. |
| 5,258,546 | A | 11/1993 | Klusener et al. |
| 5,436,356 | A | 7/1995 | Drent et al. |
| 5,563,308 | A | 10/1996 | Spindler et al. |
| 5,710,344 | A * | 1/1998 | Breikss et al. .............. 568/454 |
| 5,760,264 | A | 6/1998 | Brieden |
| 5,783,715 | A | 7/1998 | Pugin |
| 5,962,732 | A | 10/1999 | Burke |
| 6,015,919 | A | 1/2000 | Pugin |
| 6,156,934 | A | 12/2000 | Suykerbuyk et al. |
| 6,169,192 | B1 | 1/2001 | Pugin et al. |
| 6,191,284 | B1 | 2/2001 | Knochel et al. |
| 6,258,979 | B1 | 7/2001 | Kagan et al. |
| 6,284,919 | B1 | 9/2001 | Pearson et al. |
| 6,284,925 | B1 | 9/2001 | Knochel et al. |
| 6,307,065 | B1 | 10/2001 | Tjaden et al. |
| 6,335,471 | B1 * | 1/2002 | Eastham et al. ............... 568/17 |
| 6,337,406 | B1 | 1/2002 | Zhang |
| 6,348,621 | B1 | 2/2002 | Eastham et al. |
| 6,391,818 | B1 | 5/2002 | Bonsel et al. |
| 6,462,095 | B1 | 10/2002 | Bonsel et al. |
| 6,476,255 | B1 | 11/2002 | Hadden et al. |
| 6,521,769 | B1 | 2/2003 | Zhang |
| 6,706,912 | B2 | 3/2004 | Drent et al. |
| 6,723,882 | B2 | 4/2004 | Slany et al. |
| 6,743,911 | B2 | 6/2004 | Drent et al. |
| 6,753,450 | B2 | 6/2004 | Ahlers et al. |
| 6,916,954 | B2 | 7/2005 | Schafer et al. |

(Continued)

FOREIGN PATENT DOCUMENTS

DE      19745904 A1      4/1999

(Continued)

OTHER PUBLICATIONS

Wang et al., "Polymer-Bound Bidentate-Phosphine-Pallalium Complex As A Catalyst In The Heck Arylation", J. Org. Chem, 1994, pp. 5358-5364, vol. 59, No. 18.

(Continued)

*Primary Examiner*—Sikarl A Witherspoon
(74) *Attorney, Agent, or Firm*—Venable LLP; Keith G. Haddaway; Michael E. Nelson

(57) ABSTRACT

The present invention provides a process for the hydroformylation of ethylenically unsaturated compounds, which process comprises reacting said ethylenically unsaturated compound with carbon monoxide and hydrogen, in the presence of a catalyst system and a solvent, the catalyst system obtainable by combining: a) a metal of Group VIII or a compound thereof; and b) a bidentate phosphine, the process characterized in that a chlorine moiety is present in at least one of the said Group VIII metal compound or said solvent.

61 Claims, No Drawings

U.S. PATENT DOCUMENTS

| | | | |
|---|---|---|---|
| 6,982,357 | B2 | 1/2006 | Crabtree et al. |
| 6,984,668 | B1 | 1/2006 | Eastham et al. |
| 7,026,473 | B2 | 4/2006 | Drent et al. |
| 7,148,176 | B2 | 12/2006 | Beller et al. |
| 7,265,240 | B2 | 9/2007 | Eastham et al. |
| 7,371,705 | B2 | 5/2008 | Eastham et al. |
| 2001/0051745 | A1 | 12/2001 | Pearson et al. |
| 2002/0045748 | A1 | 4/2002 | Drent et al. |
| 2003/0191339 | A1 | 10/2003 | Schfer et al. |
| 2004/0162440 | A1 | 8/2004 | Bunel et al. |
| 2005/0090694 | A1 | 4/2005 | Drent et al. |
| 2006/0106259 | A1 | 5/2006 | Eastham et al. |
| 2006/0122435 | A1 | 6/2006 | Eastham et al. |
| 2006/0128985 | A1 | 6/2006 | Eastham et al. |
| 2006/0252935 | A1 | 11/2006 | Eastham et al. |
| 2008/0086015 | A1 | 4/2008 | Eastham |

FOREIGN PATENT DOCUMENTS

| | | |
|---|---|---|
| DE | 19754304 A1 | 6/1999 |
| DE | 10023470 A1 | 11/2001 |
| DE | 10037961 A1 | 2/2002 |
| EP | 0055875 | 7/1982 |
| EP | 0106379 | 4/1984 |
| EP | 0144118 | 6/1985 |
| EP | 0227160 | 7/1987 |
| EP | 0235864 | 9/1987 |
| EP | 0274795 | 7/1988 |
| EP | 0282142 | 9/1988 |
| EP | 0305089 A1 | 3/1989 |
| EP | 0375573 A1 | 6/1990 |
| EP | 0386833 | 9/1990 |
| EP | 0441447 | 8/1991 |
| EP | 0489472 | 6/1992 |
| EP | 0495347 A1 | 7/1992 |
| EP | 0495348 A1 | 7/1992 |
| EP | 0495547 A2 | 7/1992 |
| EP | 0495548 | 7/1992 |
| EP | 0499329 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1330309 A1 | 7/2003 |
| FR | 2034147 | 12/1970 |
| GB | 2006208 A | 5/1979 |
| JP | 08134218 A | 5/1996 |
| WO | WO-96/19434 | 6/1996 |
| WO | WO-9708124 A1 | 3/1997 |
| WO | WO-98/41495 | 9/1998 |
| WO | WO-98/45040 | 10/1998 |
| WO | WO-9842717 | 10/1998 |
| WO | WO-99/47528 A1 | 9/1999 |
| WO | WO-00/56695 A1 | 9/2000 |
| WO | WO-01/10551 | 2/2001 |
| WO | WO-01/28972 A1 | 4/2001 |
| WO | WO-01/65583 A1 | 9/2001 |
| WO | WO-0168583 | 9/2001 |
| WO | WO-0170659 | 9/2001 |
| WO | WO-01/72697 | 10/2001 |
| WO | WO-01/85662 A2 | 11/2001 |
| WO | WO-0212161 | 2/2002 |
| WO | WO-03/040159 | 5/2003 |
| WO | WO-03/070370 A1 | 8/2003 |
| WO | WO-2004/014552 A1 | 2/2004 |
| WO | WO-2004/014834 A1 | 2/2004 |
| WO | WO-2004/024322 A2 | 3/2004 |
| WO | WO-2004/050599 A1 | 6/2004 |
| WO | WO2004/103948 | 12/2004 |
| WO | WO-2005/003070 A1 | 1/2005 |
| WO | WO-2005/079981 A1 | 9/2005 |
| WO | WO-2005/082830 | 9/2005 |
| WO | WO-2005118519 A1 | 12/2005 |
| WO | WO-006/062467 A1 | 6/2006 |
| WO | WO-2006/084892 A2 | 8/2006 |
| WO | WO-2007/119079 A1 | 10/2007 |

OTHER PUBLICATIONS

Hofmann et al., "bis(di-t-butylphosphino)methane complexes of rhodium: homogeneous alkyne hydrosilylation by catalyst-dependent alkyne insertion into rh-si or rh-h bonds. molecular structures of the dimer [(dtbpm) rhcl]$_2$ and of the silyl complex (dtbpm) rh[si(oet)$^{3}$]$^{(pme}$ 3)", Journal of Organometallic Chemistry, 1995, pp. 51-70, vol. 490.

Lindner et al., "Catalytic Activity Of Cationic Diphosopalladium (Ii) Complexes In The Alkene/Co Copolymerization In Organic Solvents And Water In Dependence On The Length Of The Alkyl Chain At The Phosphine Ligands", Journal of Organometallic Chemistry, 2000, pp. 173-187, vol. 602.

Richmond et al., "Preparation Of New Catalysts By The Immobilization Of Palladium(Ii) Species Onto Silica: An Investigation Of Their Catalytic Activity For The Cyclization Of Aminoalkynes", J. Am Chem. Soc., 2001, pp. 10521-10525, vol. 123.

Tamao et al., "Alkyl Group Isomerization in the Cross-Coupling Reaction Of Secondary Alkyl Grignard Reagents With Organic Halides In The Presence Of Nickel-Phosphine Complexes As Catalysts", Journal of the American Chemical Society, 1972, pp. 9268-9269, vol. 94.

Jones et al, "Rhodium-Catalyzed Activation And Functionalization Of The C-C Bond Of Biphenylene", Organometallics, 2001, pp. 5745-5750. vol. 20.

"Highly active [Pd(AcO)$_2$(dppp(] catalyst for the CO-C$_2$H$_4$ copolymerization in H$_2$O-CH$_3$COOH solvent [dppp = 1,3-bis (diphenylphosphino)propane]" Andrea Vavasori et al., Journal of Molecular Cat. A. Chem., vol. 204-205, 2003, pp. 295-303.

"Hydroesterification of styrene using an in situ formed Pd(OTs)$_2$(PPh$_3$)$_2$ complex catalyst", A. Seayad et al., Journal of Molecular Cat. A. Chem., vol. 151, 2000, pp. 47-59.

"Carbon monoxide-ethylene copolymerization catalyzed by a Pd(AcO)$_2$/dpppTsOH[1] system: the promoting effect of water and of the acid", Journal of Molecular Cat. A. Chem., vol. 110, 1996, pp. 13-23.

Kirk Othmer Encyclopaedia of Chemical Terminology, vol. 9, 4th Ed., p. 783, Hydrolysis of Organic Esters, pp. 783-785 and 787, John Wiley & Sons, Jan. 1994.

Masters, Christopher, "Homogeneous Transition Metal Catalysis," p. 4-21, Chapman and Hall, Feb. 1981.

Lide et al., Handbook of Chem and Phys., 76th Ed., CRC Press, 1995, ps. 8-141 6-155 to 6-177; 15-16 to 15-25.

Clegg, W. et al: "Highly active and selective catalysts for the production of methl propanoate via the methoxycarbonylation of ethene" Chem. Commun., 1999, pp. 1877-1878.

Juian G. Knight et al: "Remarkable Differences in Catalyst Activity and Selectivity fo rthe production of Methyl Propanoate versus CO-Ethylene Copolymer by a Series of palladium Complexes of Related C$_4$-Bridged Diphosphines" Organometallics 2000, 19 4957-4967.

Adam J. Rucklidge et al.: "Methoxycarbonylation f vinyl acetate catalysed by palladium comlexes of bis ) ditertiarybutylphosphinomethyl) benzene and related ligands" Chem. Commun., 2005, pp. 1176-1178.

Brunkan et al. "Effect of chiral cavities associated with molecularly imprinted platinum centers on the selectivity of ligand-exchange reactions at platinum", Journal of American Chemical Society, No. 22, pp. 6217-6225, (2000).

Brunkan et al. "Unorthodox C,O binding mode of Me2BINOL in Pt(II) complexes", Journal of American Chemical Society, No. 120, pp. 11002-11003, (1998).

Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).

Hartwig, et al. "Structure and reactions of oxametallacyclobutanes and oxametallacyclobutenes of ruthenium", Organometallics, vol. 10, No. 9, pp. 3344-3362 (1991).

Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).

Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., issue 1, pp. xvii-xx. (1989).

Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).

Hayward et al. "Some reactions of peroxobis(triphenylphosphine)platinum(II) and analogs with carbon dioxide, carbon disulfide, and other unsaturated molecules", Journal of American Chemical Society, vol. 92, issue 20, pp. 5873-5878, (1970).

Osman, Serindag "Synthesis of some platinum(II) diphosphine complexes of the type [$PtX_2$(P-P)] ($X_2 = CO_3$; X = $CH_3COO$, $CF_3COO$, NCO)", Synth. React. Inorg. Met.-Org. Chem., vol. 27. No. 1, pp. 69-76, (1997).

Andrews et al. "Syntheses, spectra and structures of (diphosphine)platinum(II) carbonate complexes" Inorganic Chemistry, No. 35, pp. 5478-5483, (1996).

Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).

Becker et al. "Synthesis and characterization of chiral diphosphine platinum(II) VANOL and VAPOL complexes", Organometallics, No. 22, pp. 3245-3249, (2003).

Becker et al. "Imprinting chiral information into rigidified dendrimers", Organometallics, No. 22, pp. 4984-4998, (2003).

Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).

Wen et al. "Synthesis, resolution, and applications of 1,16-dihydroxytetraphenylene as a novel building block in molecular recognition and assembly", Journal of Organic Chemistry, No. 68, pp. 8918-8931, (2003).

Mikami et al. "Molecular design of DABNTf as a highly efficient resolving reagent for racemic Pd complex with tropos biphenylphosphine (BIPHEP) ligand: circular dichroism (CD) spectra of enantiopure BIPHEP-Pd complex", Chirality, No. 15, pp. 105-107, (2003).

Tudor et al. "Diasteroisomer interconversion in chiral Biphep$PtX_2$ complexes", Organometallics, No. 19, pp. 4376-4384, (2000).

Bellabarba et al., "Synthesis, X-ray characterization and reactions of a trigonal planar palladium()) carbonyl complex", Chemical Communications, No. 15, pp. 1916-1917, (2003).

Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).

Clegg et al., "Characterisation and dynamics of [Pd(L-L)H(solv)]+, [Pd(L-L(CH2CH3)]+ and [Pd(L-L)(C(0)Et)(THF)]+ (L-L = 1,2-(CH2PBut2)2C6H4): key intermediates in the catalytic methoxycarbonylation of ethane to methylpropanoate", Organometallics, vol. 21, No. 9, pp. 1832-1840 (2002).

Edelbach et al., "Catalytic hydrogenolysis of biphenylene with platinum, palladium, and nickelphosphine complexes", Organometallics, vol. 17, No. 22, pp. 4784-4794 (1998).

Kim et al., "Synthesis and theoretical study of palladium (II) complexes with aminophosphines as 7-membered chelate rings", Bulletin of the Korean Chemical Society, vol. 18, No. 11, pp. 1162-1166 (1997).

Reddy et al., "Unexpected cross-metathesis between Si-C and Si-Si bonds", Chemical Communications, No. 16, pp. 1865-1866 (1996).

Uchimaru et al., "Ring-opening polymerization of 1,1,2,2-tetramethyl-1,2-disilacyclopentane via palladium complex-catalysed Si-Si bond metathesis", Chemistry Letters, No. 2, p. 164 (1995).

Portnoy et al., "Reactions of electron-rich arylpalladium complexes with olefins. Origin of the chelate effect in vinylation catalysis", Organometallics, vol. 13, No. 9, pp. 3465-3479 (1994).

Wurst et al., "Synthesis and structure of the platinum (0) compounds [(dipb)Pt]2(COD) and (dipb)3Pt2 and of the cluster Hg6[Pt(dipb)]4 (dipb = (iPr)2P(CH2)4P(i-Pr)2)", Zeitschrift Für Anorganische Und Allgemeine Chemie, vol. 395, pp. 239-250 (1991).

Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).

Molander et al., "Synthesis and application of chiral cyclopropane-based ligands in palladium-catalyzed allylic alkylation", Journal of Organic Chemistry, vol. 69, No. 23, pp. 8062-8069 (2004).

Brauer et al., "Reactions of coordinated ligands. XIV. Synthesis of a tetradentate phosphorus macrocycle in a palladium (II) template", Chemische Berichte, vol. 119, No. 1, pp. 349-365 (1986).

Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).

Pugh, R. I. et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (Aug. 21, 2001), pp. 1476-1477.

Cullen et al, "Structure of the Hydrogenation Catalyst [(PP)Rh(NBD)]ClO4, (PP) = ( 5-[(CH3)3C]2PC5H4)2Fe, and Some Comparative Rate Studies," Organometallics, vol. 2, pp. 714-719, 1983.

Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.

Related U.S. Appl. No. 10/524,023, filed Nov. 17, 2005, Eastham et al.

Olah, George A., et al., "$AlCl_3$-Catalyzed Dichlorophosphorylation of Saturated Hydrocarbons with $PCl_3$ in Methylene Chloride Solution," J. Org. Chem., 1990, 55, 1224-1227.

Wei-Yong Yu, et al.,"Preparation of Polymer-Protected Pt/Co Bimetallic Colloid and its Catalytic Properties in Selective Hydrogenation of Cinnamaldehyde to Cinnamyl Alcohol," Polymers For Advanced Technologies, GB, John Wiley and Sons, Chichester, Aug. 1, 1996, 719-722, Vol. 7, No. 8.

Tolman, "Phosphorous Ligand Exchange Equilibria on Zerovalent Nickel. A Dominant Role for Steric Effects," Journal of the American Chemical Society, vol. 92, No. 10, pp. 2956-2965, 1970.

Tolman, "Steric Effects of Phosphorous Ligands in Organometallic Chemisty and Homogeneous Catalysis," Chemical Reviews, vol. 77, No. 3, pp. 313-348, 1977.

Grimmer, et al., "Zirconium bis-cyclopentadienyl compounds: An investigation into the influence of substituent effects on the ethene polymerisation behaviour of $(CpR)_2ZrCl_2$/MAO catalysts," Journal of Molecular Catalysis A: Chemical, vol. 188, No. 1-2, pp. 105-113, 2002.

Machine Translation of JP 08-134218, May 28, 1996.

Office Action for U.S. Appl. No. 11/597,787, issued by the USPTO on Oct. 8, 2008.

Office Action for U.S. Appl. No. 11/597,787, issued by the USPTO on May 20, 2009.

Office Action for U.S. Appl. No. 10/536,801, issued by the USPTO on Apr. 8, 2008.
Office Action for U.S. Appl. No. 10/536,801, issued by the USPTO on Jan. 7, 2010.

Office Action for U.S. Appl. No. 10/536,801, issued by the USPTO on Jun. 17, 2009.

* cited by examiner

PROCESS FOR THE HYDROFORMYLATION OF ETHYLENICALLY UNSATURATED COMPOUNDS

The present invention relates to the hydroformylation of ethylenically unsaturated compounds by reaction with carbon monoxide and hydrogen in the presence of a catalyst system.

The carbonylation and hydroformylation of ethylenically unsaturated compounds using carbon monoxide in the presence of hydrogen and a catalyst comprising a group VIII metal, example, rhodium, and a phosphine ligand, example an alkyl phosphine, cycloalkyl phosphine, aryl phosphine, pyridyl phosphine or bidentate phosphine, has been described in numerous patents and patent applications.

WO 96/19434 disclosed that a particular group of bidentate phosphine compounds can provide stable catalysts in carbonylation reaction systems, and the use of such catalysts leads to reaction rates which were significantly higher than those previously disclosed.

WO 01/68583 discloses carbonylation processes for higher alkenes of three or more carbon atoms.

WO 02/76996, for example, discloses a method for producing diphosphines, and their use as co-catalyst for hydroformylating olefins. WO 02/20448 similarly discloses the preparation of arylphosphines for the rhodium-catalysed hydroformylation of alkenes.

Although catalyst systems have been developed which exhibit reasonable stability during the hydroformylation process and permit relatively high reaction rates and regioselectivity between linear and branched aldehyde products, there still exists a need for alternative and/or improved catalyst systems. Suitably, the present invention aims to provide an alternative and/or improved catalyst for hydroformylating ethylenically unsaturated compounds. Moreover, the present invention aims to provide solvents which improve the performance of the catalyst system.

Surprisingly, it has been found that improved selectivity of the linear aldehyde product compared to the branched aldehyde product can be obtained than by using comparative catalyst systems of the prior art.

According to the present invention there is provided a process for the hydroformylation of ethylenically unsaturated compounds, as set forth in the appended claims. Preferred features of the invention will be apparent from the dependent claims, and the description. Also according to the present invention there is provided a catalyst system, a hydroformylation reaction catalyst system, a reaction medium, a hydroformylation reaction medium, use of a catalyst system, use of a reaction medium, and a process for preparing a catalyst system and reaction medium, as set forth hereinafter and in the appended claims.

According to the first aspect of the present invention there is provided a process for the hydroformylation of ethylenically unsaturated compounds, which process comprises reacting said ethylenically unsaturated compound with carbon monoxide and hydrogen, in the presence of a catalyst system and a solvent, the catalyst system obtainable by combining:

a) a metal of Group VIII or a compound thereof; and
b) a bidentate phosphine of general formula (Ia)

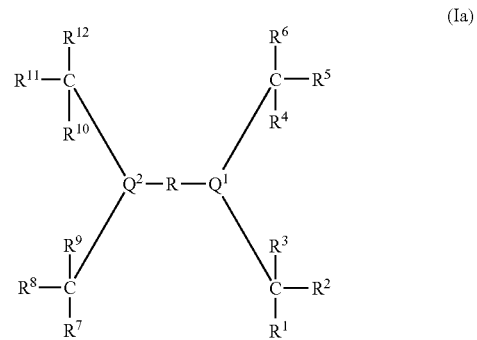

(Ia)

wherein R is a covalent bridging group;
$R^1$ to $R^{12}$ each independently represent hydrogen, lower alkyl, aryl or Het, preferably, lower alkyl, aryl or Het;
$Q^1$ and $Q^2$ each independently represent phosphorus, arsenic or antimony and in the latter two cases references to phosphine or phosphorus above are amended accordingly, the process characterised in that a chlorine moiety is present in at least one of the said Group VIII metal compound or said solvent.

Such a process is referred to hereinafter as "the process of the invention". The process of the invention includes the embodiments set out hereinafter.

In one set of embodiments, the group R in formula (Ia) may represent an alkylene bridging group, preferably, a lower alkylene.

In another and preferred set of embodiments, the bridging group R may be defined as -A-(K,D)Ar(E,Z)—B—, such that general formula (Ia) becomes general formula (I),

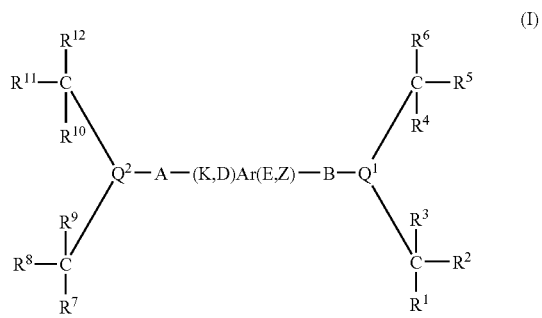

(I)

wherein:
Ar is a bridging group, comprising an optionally substituted aryl moiety to which the phosphorus atoms are linked on available adjacent carbon atoms;
A and B each independently represent lower alkylene;
K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15}))R^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;

$R^1$ to $R^{18}$ each independently represent hydrogen, lower alkyl, aryl, or Het, preferably, lower alkyl, aryl or Het;

$R^{19}$ to $R^{27}$ each independently represent hydrogen, lower alkyl, aryl or Het;

$Q^1$, $Q^2$ and $Q^3$ (when present) each independently represent phosphorous, arsenic or antimony and in the latter two cases references to phosphine or phosphorous above are amended accordingly.

Preferably, when K, D, E or Z represent $-J-Q^3(CR^{13}(R^{14})(R^{15}))CR^{16}(R^{17})(R^{18})$, the respective K, D, E or Z is on the aryl carbon adjacent the aryl carbon to which A or B is connected or, if not so adjacent, is adjacent a remaining K, D, E or Z group which itself represents $-J-Q^3(CR^{13}(R^{14})(R^{15})CR^{16}(R^{17})(R^{18})$.

Preferably, $R^1$ to $R^{18}$ each independently represent lower alkyl or aryl. More preferably, $R^1$ to $R^{18}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^{18}$ each independently represent $C_1$ to $C_6$ alkyl, which is optionally substituted as defined herein. Most preferably, $R^1$ to $R^{18}$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^1$ to $R^3$, $R^4$ to $R^6$, $R^7$ to $R^9$, $R^{10}$ to $R^{12}$, $R^{13}$ to $R^{15}$ or $R^{16}$ to $R^{18}$ together independently may form cyclic structures such as 1-norbornyl or 1-norbornadienyl. Further examples of composite groups include cyclic structures formed between $R^1$ to $R^6$, $R^7$ to $R^{12}$, and $R^{13}$ to $R^{18}$. Alternatively, one or more of the groups may represent a solid phase to which the ligand is attached.

Moreover, at least one $(CR^xR^yR^z)$ group attached to $Q^1$ and/or $Q^2$, i.e. $CR^1R^2R^3$, $CR^4R^5R^6$, $CR^7R^8R^9$, or $CR^{10}R^{11}R^{12}$, may instead be congressyl or adamantyl, or both groups defined above as $(CR^xR^yR^z)$ attached to either or both $Q^1$ and/or $Q^2$, may, together with either $Q^1$ or $Q^2$ as appropriate, instead form an optionally substituted 2-phospha-tricyclo[3.3.1.1{3,7}]decyl group or derivative thereof. However, in this particular set of embodiments, i.e. when the bridging group is defined as -A-(K,D)Ar(E,Z)—, if any $(CR^xR^yR^z)$ groups are defined as per this paragraph, they are preferably congressyl or adamantyl, more preferably non-substituted adamantyl or congressyl, most preferably a non-substituted adamantyl group.

In a particularly preferred embodiment of the present invention $R^1$, $R^4$, $R^7$, $R^{10}$, $R^{13}$ and $R^{16}$ each represent the same lower alkyl, aryl or Het moiety as defined herein, $R^2$, $R^5$, $R^8$, $R^{11}$, $R^{14}$ and $R^{17}$ each represent the same lower alkyl, aryl or Het moiety as defined herein, and $R^3$, $R^6$, $R^9$, $R^{12}$, $R^{15}$ and $R^{18}$ each independently represent the same lower alkyl, aryl or Het moiety as defined herein. More preferably $R^1$, $R^4$, $R^7$, $R^{10}$, $R^{13}$ and $R^{16}$ each independently represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$, $R^{11}$, $R^{14}$ and $R^{17}$ each independently represent the same $C_1$-$C_6$ alkyl as defined above; and $R^3$, $R^6$, $R^9$, $R^{12}$, $R^{15}$ and $R^{18}$ each independently represent the same $C_1$-$C_6$ alkyl as defined above. For example: $R^1$, $R^4$, $R^7$, $R^{10}$, $R^{13}$ and $R^{16}$ each represent methyl; $R^2$, $R^5$, $R^8$, $R^{11}$, $R^{14}$ and $R^{17}$ each represent ethyl; and, $R^3$, $R^6$, $R^9$, $R^{12}$, $R^{15}$ and $R^{18}$ each represent n-butyl or n-pentyl.

In an especially preferred embodiment of the present invention each $R^1$ to $R^{18}$ group represents the same lower alkyl, aryl, or Het moiety as defined herein. Preferably, each $R^1$ to $R^{18}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably, each $R^1$ to $R^{18}$ represents methyl.

In the compound of formula (I), preferably each $Q^1$, $Q^2$ and $Q^3$ (when present) is the same. Moreover, in a compound of formula (Ia), preferably $Q^1$ and $Q^2$ are the same. Most preferably, each $Q^1$, $Q^2$ and $Q^3$ (when present) represents phosphorous.

Preferably, in the compound of formula (I), A, B and J (when present) each independently represent $C_1$ to $C_6$ alkylene which is optionally substituted as defined herein, for example with lower alkyl groups. Moreover, in the compound of formula (Ia), R (when alkylene) represents $C_1$ to $C_6$ alkylene which is optionally substituted as defined herein, for example with lower alkyl groups. Preferably, the lower alkylene groups which A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—. Particularly preferred lower alkylenes which R represents are substituted or non-substituted and may be selected from ethylene (—$C_2H_4$—), and substituted-variants thereof, propylene (—$C_4H_6$—), and substituted variants thereof, and butylene (—$C_4H_8$—), and substituted variants thereof, and wherein such substitution may be on any, some or all of the carbon atoms of the lower alkylene and such substitution may be with lower alkyl groups. More preferably, the lower alkylenes which R represents are substituted or non-substituted ethylene or propylene, most preferably, substituted or non-substituted propylene.

Preferably, in the compound of formula (I) when K, D, E or Z does not represent $-J-Q^3(CR^{13}(R^{14})(R^{15}))CR^{16}(R^{17})(R^{18})$, K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E or Z represents hydrogen.

Preferably, in the compound of formula (I) when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula (I) when K, D, E or Z does not represent $-J-Q^3(CR^{13}(R^{14})(R^{15}))CR^{16}(R^{17})(R^{18})$ and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1$-$C_6$ alkyl (more particularly unsubstituted $C_1$-$C_6$ alkyl), especially hydrogen.

Preferably, in the compound of formula (I) when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula (I) within this set of embodiments include those wherein:

A and B each independently represent unsubstituted $C_1$ to $C_6$ alkylene;

K, D, Z and E each independently represent hydrogen, $C_1$-$C_6$ alkyl, phenyl, $C_1$-$C_6$ alkylphenyl or -J-$Q^3$($CR^{13}(R^{14})(R^{15})$)$CR^{16}(R^{17})(R^{18})$ where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.

$R^1$ to $R^{18}$ each independently represent $C_1$ to $C_6$ alkyl, phenyl or $C_1$ to $C_6$ alkylphenyl.

Further preferred compounds of formula (I) within this set of embodiments include those wherein:

A and B both represent —$CH_2$— or $C_2H_4$, particularly $CH_2$;

K, D, Z and E each independently represent hydrogen, $C_1$-$C_6$ alkyl phenyl or $C_1$-$C_6$ alkyl or -J-$Q^3$($CR^{13}(R^{14})(R^{15})$)$CR^{16}(R^{17})(R^{18})$ where J is the same as A; or two of K, D, E and Z together with the carbon atoms of the aryl ring to which they are attached form an unsubstituted phenyl ring;

$R^1$ to $R^{18}$ each independently represent $C_1$ to $C_6$ alkyl;

Still further preferred compounds of formula (I) within this set of embodiments include those wherein:

$R^1$ to $R^{18}$ are the same and each represents $C_1$ to $C_6$ alkyl, particularly methyl.

Still further preferred compounds of formula I within this set of embodiments include those wherein:

K, D, Z and E are each independently selected from the group consisting of hydrogen or $C_1$ to $C_6$ alkyl, particularly where each of K, D, Z and E represent the same group, especially where each of K, D, Z and E represent hydrogen; or K represents —$CH_2$-$Q^3$($CR^{13}(R^{14})(R^{15})$)$CR^{16}(R^{17})(R^{18})$ and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula (I) within this set of embodiments include those wherein:

each $R^1$ to $R^{12}$ is the same and represents methyl;

A and B are the same and represent —$CH_2$—;

K, D, Z and E are the same and represent hydrogen.

In this particular set of embodiments, Ar may be defined as are "Ar" and "aryl" hereinafter, but preferably, Ar is defined as including six-to-ten-membered carbocyclic aromatic groups, such as phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}$, $R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined hereinafter).

In a further set of embodiments, in a compound of either formula (I) or (Ia) at least one ($CR^xR^yR^z$) group attached to $Q^1$ and/or $Q^2$, i.e. $CR^1R^2R^3$, $CR^4R^5R^6$, $CR^7R^8R^9$, or $CR^{10}R^{11}R^{12}$, may instead be congressyl or adamantyl, or both groups defined above as ($CR^xR^yR^z$) attached to either or both $Q^1$ and/or $Q^2$, may, together with either $Q^1$ or $Q^2$ as appropriate, instead form an optionally substituted 2-phospha-tricyclo[3.3.1.1{3,7}]decyl group or derivative thereof, preferably the at least one ($CR^xR^yR^z$) group being congressyl or adamantyl.

The adamantyl group may optionally comprise, besides hydrogen atoms, one or more substituents selected from lower alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)(R^{27})R^{28}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$ (defined as are $R^{19}$ to $R^{27}$ hereinbefore), lower alkyl, cyano and aryl are as defined herein and $R^{56}$ to $R^{62}$ each independently represent hydrogen, lower alkyl, aryl or Het. However, in one embodiment, the adamantyl groups are not substituted.

Suitably, when the adamantyl group is substituted with one or more substituents as defined above, highly preferred substituents include unsubstituted $C_1$ to $C_8$ alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, —$C(O)N(R^{25})R^{26}$ and —$PO(R^{58})(R^{59})$, —$CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{59}$ each independently represent unsubstituted $C_1$-$C_8$ alkyl or phenyl.

Suitably, the adamantyl group may comprise, besides hydrogen atoms, up to 10 substituents as defined above, preferably up to 5 substituents as defined above, more preferably up to 3 substituents as defined above. Suitably, when the adamantyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl group comprises hydrogen atoms only i.e. the adamantyl group is not substituted.

Preferably, when more than one adamantyl group is present in a compound of formula (Ia) or (I), each adamantyl group is identical.

The 2-phospha-tricyclo[3.3.1.1.{3,7}]decyl group (referred to as 2-phospha-adamantyl group herein) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-phospha-adamantyl group includes more than one substituent, preferably each substituent is identical.

Preferably, the 2-phospha-adamantyl group is substituted on one or more of the 1, 3, 5 or 7 positions with a substituent as defined herein. More preferably, the 2-phospha-adamantyl group is substituted on each of the 1, 3 and 5 positions. Suitably, such an arrangement means the phosphorous atom of the 2-phospha-adamantyl group is bonded to carbon atoms in the adamantyl skeleton having no hydrogen atoms. Most preferably, the 2-phospha-adamantyl group is substituted on each of the 1, 3, 5 and 7 positions. When the 2-phospha-adamantyl group includes more than 1 substituent preferably each substituent is identical. Especially preferred substituents are unsubstituted $C_1$-$C_8$ alkyl and trifluoromethyl, particularly unsubstituted $C_1$-$C_8$ alkyl such as methyl.

Preferably, 2-phospha-adamantyl represents unsubstituted 2-phospha-adamantyl or 2-phospha-adamantyl substituted with one or more unsubstituted $C_1$-$C_8$ alkyl substituents, or a combination thereof.

Preferably, the 2-phospha-adamantyl group includes additional heteroatoms, other than the 2-phosphorous atom, in the 2-phospha-adamantyl skeleton. Suitable additional heteroatoms include oxygen and sulphur atoms, especially oxygen atoms. More preferably, the 2-phospha-adamantyl group includes one or more additional heteroatoms in the 6, 9 and 10 positions. Even more preferably, the 2-phospha-adamantyl group includes an additional heteroatom in each of the 6, 9 and 10 positions. Most preferably, when the 2-phospha-adamantyl group includes two or more additional heteroatoms in the 2-phospha-adamantyl skeleton, each of the additional heteroatoms are identical. An especially preferred 2-phospha-adamantyl group, which may optionally be substituted with one or more substituents as defined herein, includes an oxygen atom in each of the 6, 9 and 10 positions of the 2-phospha-adamantyl skeleton.

Preferably, the 2-phospha-adamantyl includes one or more oxygen atoms in the 2-phospha-adamantyl skeleton.

Highly preferred 2-phospha-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most, preferably the 2-phospha-adamantyl is selected from 2-phospha-1,3,5,7-tetramethyl-6,9,10-trioxadamantyl group or 2-phospa-1,3,5,-trimethyl-6,9,10-trioxadamantyl group.

Preferably, when more than one 2-phospha-adamantyl group is present in a compound of formula (I) or (Ia), each 2-phospha-adamantyl group is identical.

The 2-phospha-adamantyl group may be prepared by methods well known to those skilled in the art. Suitably, certain 2-phospha-adamantyl compounds are obtainable from Cytec Canada Inc of 901 Garner Road, Niagara Falls, Ontario, Canada L2E 6T4. Likewise corresponding 2-phospha-adamantyl compounds of formula (I) etc may be prepared by analogous methods.

Moreover, at least one of $CR^{13}(R^{14})(R^{15})$ and $CR^{16}(R^{17})(R^{18})$, when present, may instead be congressyl or adamantyl, optionally substituted as described above, or both groups defined as $CR^{13}(R^{14})(R^{15})$ and $CR^{16}(R^{17})(R^{18})$ attached to $Q^3$, may together with $Q^3$, instead form an optionally substituted 2-phospha-tricyclo[3.3.1.1{3,7}]decyl group or derivative thereof, preferably the at least one of $CR^{13}(R^{14})(R^{15})$ and $CR^{16}(R^{17})(R^{18})$, when present, being congressyl or adamantyl.

Preferably, in a compound of formula (I) when both K represents $-J-Q^3(CR^{13}(R^{14})(R^{15}))CR^{16}(R^{17})(R^{18})$ and E represents $-J-Q^3(CR^{13}(R^{14})(R^{15})CR^{16}(R^{17})(R^{18})$, then D represents $-J-Q^3(CR^{13}(R^{14})(R^{15}))CR^{16}(R^{17})(R^{19})$.

By the term 2-phospha-tricyclo[3.3.1.1{3,7}]decyl group we mean a 2-phospha-adamantyl group formed by the combination of the two groups attached to $Q^1$, together with $Q^1$ to which they are attached, a 2-phospha-adamantyl group formed by the combination of the two groups attached to $Q^2$, together with $Q^2$ to which they are attached, a 2-phospha-adamantyl group formed by the combination of the two groups attached to $Q^3$, together with $Q^3$ to which they are attached, wherein $Q^1$, $Q^2$, or $Q^3$ is in the 2-position of the adamantyl group of which it forms an integral part and each of $Q^1$, $Q^2$, and $Q^3$ represents phosphorus.

Preferred compounds within the present set of embodiments and wherein at least one 2-phospha-adamantyl group is present include those wherein:

Groups $CR^1(R^2)(R^3)$ and $CR^4(R^5)(R^6)$ are attached to $Q^1$, and the groups attached to $Q^2$, together with $Q^2$, form a 2-phospha-adamantyl group;

Groups $CR^1(R^2)(R^3)$ and adamantyl are attached to $Q^1$, and the groups attached to $Q^2$, together with $Q^2$, form a 2-phospha-adamantyl group;

Groups $CR^1(R^2)(R^3)$ and congressyl are attached to $Q^1$, and the groups attached to $Q^2$, together with $Q^2$, form a 2-phospha-adamantyl group;

Two adamantyl groups are attached to $Q^1$, and the groups attached to $Q^2$, together with $Q^2$ form a 2-phospha-adamantyl group;

Two congressyl groups are attached to $Q^3$, and the groups attached to $Q^2$, together with $Q^2$, form a 2-phospha-adamantyl group;

The groups attached to $Q^1$, together with $Q^3$, form a 2-phospha-adamantyl group, and the two groups attached to $Q^2$, together with $Q^2$, form a 2-phospha-adamantyl group.

Naturally, in the preferred compounds noted above, $Q^1$ and $Q^2$ can be interchanged, together with the groups attached thereto. Therefore, for example, the first preferred compound in the list could equally preferably be:

Groups $CR^7(R^8)(R^9)$ and $CR^{10}(R^{11})(R^{12})$ are attached to $Q^2$, and the groups attached to $Q^1$, together with $Q^1$, form a 2-phospha-adamantyl group.

Highly preferred compounds within this embodiment include those wherein:

The groups attached to $Q^1$, together with $Q^1$, form a 2-phospha-adamantyl group, and the two groups attached to $Q^2$, together with $Q^2$, form a 2-phospha-adamantyl group.

Preferably, the groups attached to $Q^1$ are identical.

Preferably, the groups attached to $Q^1$ are identical, the groups attached to $Q^2$ are identical, and the groups attached to $Q^3$ are identical, more preferably, all such groups are identical or form with the Q they are attached to, identical groups.

Particularly preferred combinations in the present invention include those of formula (I) wherein:

(1) $(CR^7R^8R^9)$ and $(CR^{10}R^{11}R^{12})$ together with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
A and B are the same and represent —$CH_2$—;
K, D and E are the same and represent hydrogen or unsubstituted $C_1$-$C_6$ alkyl, particularly hydrogen;
$Q^1$ and $Q^2$ both represent phosphorus.

(2) $(CR^7R^8R^9)$ and $(CR^{10}R^{11}R^{12})$ together with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
K represents —$CH_2$-$Q^3(X^5)X^6$ wherein $X^5$ and $X^6$ together with $Q^3$ to which they are attached represents 2-phospha-adamantyl;
A and B are the same and represent —$CH_2$—;
$Q^1$, $Q^2$ and $Q^3$ each represent phosphorus;
D and E are the same and represent hydrogen or unsubstituted $C_1$-$C_6$ alkyl, particularly hydrogen.

(3) $(CR^7R^8R^9)$ and $(CR^{10}R^{11}R^{12})$ together, with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
K represents —$CH_2$-$Q^3(X^5)X^6$ wherein $X^5$ and $X^6$ together with $Q^3$ to which they are attached represents 2-phospha-adamantyl;
A and B are the same and represent —$CH_2$—;
$Q^1$, $Q^2$ and $Q^3$ each represent phosphorus.

In a further set of embodiments, in formula (I), Ar is a cyclopentadienyl group, and Z may be represented by -$M(L_1)_n(L_2)$ m and Z is connected via a metal ligand bond to the cyclopeintadienyl group, M represents a Group VIB or VIIIB metal or metal cation thereof; and $L_1$ represents a cyclopentadienyl, indenyl or aryl group each of which groups are optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$— or ferrocenyl;

$L_2$ represents one or more ligands each of which are independently selected from hydrogen, lower alkyl, alkylaryl, halo, CO, $PR^{43}R^{44}R^{45}$ or $NR^{46}R^{47}R^{48}$;

$R^{43}$ to $R^{48}$ each independently represent hydrogen, lower alkyl, aryl or Het;

n=0 or 1;

and m=0 to 5;

provided that when n=1 then m equals 0, and when n equals 0 then m does not equal 0.

Preferably, A, B, $Q^1$, $Q^2$, K, D, E, and $R^1$ to $R^{27}$ are as defined and described hereinbefore, including preferred embodiments thereof.

By the term "M represents a Group VIB or VIIIB metal" in a compound of formula I we include metals such as Cr, Mo, W, Fe, Co, Ni, Ru, Rh, Os, Ir, Pt and Pd. Preferably, the metals are selected from Cr, Mo, W, Fe, Co, Ni, Ru and Rh. For the avoidance of doubt, references to Group VIB or VIIIB metals herein should be taken to include Groups 6, 8, 9 and 10 in the modern periodic table nomenclature.

By the term "metal cation thereof" we mean that the Group VIB or VIIIB metal (M) in the compound of formula I as defined herein has a positive charge. Suitably, the metal cation may be in the form of a salt or may comprise weakly coordinated anions derived from halo, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; perfluororated carboxylic acid such as trichloroacetic acid and trifluoroacetic acid; orthophosphoric acid; phosphonic acid such as benzene phosphonic acid; and acids derived from interactions between Lewis acids and Broensted acids. Other sources which may provide suitable anions include the tetraphenyl, borate derivatives.

Preferably M represents a Group VIB or VIIIB metal. In other words the total electron count for the metal M is 18.

Halo groups, which $L_2$ may represent and with which the above-mentioned groups may be substituted or terminated, include fluoro, chloro, bromo and iodo.

Suitably, if A represents cyclopentadienyl and n=1, the compounds of formula I may contain either two cyclopentadienyl rings, two indenyl rings or one indenyl and one cyclopentadienyl ring (each of which ring systems may optionally be substituted as described herein). Such compounds may be referred to as "sandwich compounds" as the metal M or metal cation thereof is sandwiched by the two ring systems. The respective cyclopentadienyl and/or indenyl ring systems may be substantially coplanar with respect to each other or they may be tilted with respect to each other (commonly referred to as bent metallocenes).

Alternatively, when n=1, the compounds of the invention may contain either one cyclopentadienyl or one indenyl ring (each of which ring systems may optionally be substituted as described herein) and one aryl ring (i.e. $L_1$ represents aryl) which is optionally substituted as defined herein. Suitably, when n=1 and $L_1$ represents aryl then the metal M of the compounds of formula I as defined herein is typically in the form of the metal cation.

Suitably, when n=0, the compounds of the invention contain only one cyclopentadienyl or indenyl ring (each of which ring systems may optionally be substituted as described herein). Such compounds may be referred to as "half sandwich compounds". Preferably, when n=0 then m represents 1 to 5 so that the metal M of the compounds of formula I has an 18 electron count. In other words, when metal M of the compounds of formula I is iron, the total number of electrons contributed by the ligands $L_2$ is typically five.

Suitably, the metal M or metal cation thereof in the cyclopentadienyl compounds of formula I is typically bonded to the cyclopentadienyl ring(s) or the cyclopentadienyl moiety of the indenyl ring(s). Typically, the cyclopentadienyl ring or the cyclopentadienyl moiety of the indenyl ring exhibits a pentahapto bonding mode with the metal; however other bonding modes between the cyclopentadienyl ring or cyclopentadienyl moiety of the indenyl ring and the metal, such as trihapto coordination, are also embraced by the scope of the present invention.

Preferably, in the compound of formula I wherein Ar is cyclopentadienyl, M represents Cr, Mo, Fe, Co or Ru, or a metal cation thereof. Even more preferably, M represents Cr, Fe, Co or Ru or a metal cation thereof. Most preferably, M is selected from a Group VIIIB metal or metal cation thereof. An especially preferred Group VIIIB metal (M) is Fe. Although the metal M as defined herein may be in a cationic form, preferably it carries essentially no residual charge due to coordination with $L_1$ and/or $L_2$ as defined herein.

Preferably, when n=1 in the compound of formula I, $L_1$ represents cyclopentadienyl, indenyl or aryl each of which rings are optionally substituted by one or more substituents selected from hydrogen, lower alkyl, halo, cyano, $OR^{19}$, $OC(O)R^{20}$, $C(O)R^{21}$, $C(O)OR^{22}$, $NR^{23}R^{24}$, $SR^{27}$ or ferrocenyl (by which is meant the cyclopentadienyl, indenyl or aryl ring which, $L_1$ may represent is bonded directly to the cyclopentadienyl ring of the metallocenyl group). More preferably, if the cyclopentadienyl, indenyl or aryl ring which $L_1$ may represent is substituted it is preferably substituted with one or more substituents selected, from $C_1$-$C_6$ alkyl, halo, cyano, $OR^{19}$, $OC(O)R^{20}$, $C(O)R^{21}$, $C(O)OR^{22}$, $NR^{23}R^{24}$ where $R^{19}$, $R^{20}$, $R^{21}$, $R^{22}$, $R^{23}$ and $R^{24}$ each independently represent hydrogen or $C_1$-$C_6$ alkyl.

Preferably, when n=1, $L_1$ represents cyclopentadienyl, indenyl, phenyl or naphthyl optionally substituted as defined herein. Preferably, the cyclopentadienyl, indenyl, phenyl or naphthyl groups are unsubstituted. More preferably, $L_1$ represents cyclopentadienyl, indenyl or phenyl, each of which rings are unsubstituted. Most preferably, $L_1$ represents unsubstituted cyclopentadienyl.

In a particularly preferred embodiment of the present invention, in a compound of formula I, n=1, $L_1$ is as defined herein and m=0.

Alternatively, when n is equal to zero and m is not equal to zero in a compound of formula I, $L_2$ represents one or more ligands each of which are independently selected from lower alkyl, halo, CO, $PR^{43}R^{44}R^{45}$ or $NR^{46}R^{47}R^{48}$. More preferably, $L_2$ represents one or more ligands each of which are independently selected from $C_1$ to $C_4$ alkyl, halo, particularly chloro, CO, $PR^{43}R^{44}R^{45}$ or $NR^{46}R^{47}R^{48}$, wherein $R^{43}$ to $R^{48}$ are independently selected from hydrogen, $C_1$ to $C_6$ alkyl or aryl, such as phenyl.

In a particularly preferred alternative embodiment of the present invention, in a compound of formula I, n=0, $L_2$ is as defined herein and m=3 or 4, particularly 3.

M represents a metal selected from Cr, Mo, Fe, Co or Ru or a metal cation thereof;

$L_1$ represents cyclopentadienyl, indenyl, naphthyl or phenyl, each of which rings may be optionally substituted by one or more substituents selected from $C_1$-$C_6$ alkyl, halo, cyano, $OR^{19}$, $OC(O)R^{20}$, $C(O)R^{21}$, $C(O)R^{22}$, $NR^{23}R^{24}$;

$L_2$ represents one or more ligands each of which ligands are independently selected from $C_1$-$C_6$ alkyl, halo, CO, $PR^{43}R^{44}R^{45}$ or $NR^{46}R^{47}R^{48}$;

n=0 or 1;

and m=0 to 4;

provided that when n=1 then m=0 and when m does not equal zero then n=0.

Further preferred compounds of formula I include those wherein:

M represents iron or a cation thereof;

$L_1$ represents cyclopentadienyl, indenyl or phenyl group, each of which groups are optionally substituted by one or more substituents selected from $C_1$-$C_6$ alkyl, halo, cyano, $OR^{19}$, $OC(O)R^{20}$, $C(O)R^{21}$, $C(O)R^{22}$;

$L_2$ represents one or more ligands each of which are independently selected from $C_1$-$C_6$ alkyl, halo, CO, $PR^{43}R^{44}R^{45}$ or $NR^{46}R^{47}R^{48}$, where $R^{43}$ to $R^{48}$ are independently selected from hydrogen, $C_1$-$C_6$ alkyl or phenyl;

n=0 or 1; and m=0 to 4.

Still further preferred compounds of formula I include those wherein:

$L_1$ represents unsubstituted cyclopentadienyl, indenyl or phenyl, particularly unsubstituted cyclopentadienyl; and, n=1 and m=0.

Alternative preferred compounds of formula I include those wherein:

n=0;

$L_2$ represents one or more ligands each of which are independently selected from $C_1$ to $C_6$ alkyl, halo, CO, $PR^{43}R^{44}R^{45}$ or $NR^{46}R^{47}R^{48}$, where $R^{43}$ to $R^{48}$ are independently selected from hydrogen, $C_1$-$C_6$ alkyl or phenyl; and m=1 to 4, particularly 3 or 4. For example, when m=3 the three ligands which $L_2$ may represent include $(CO)_2$halo, $(PR^{43}R^{44}R^{45})_2$halo or $(NR^{46}R^{47}R^{48})_2$halo.

Particularly preferred combinations within this embodiment of the present invention and wherein at least one 2-phospha-adamantyl group is present include those of formula (I) wherein:—

(4) $(CR^7R^8R^9)$ and $(CR^{10}R^{11}R^{12})$ together with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
A and B are the same and represent —$CH_2$—;
$Q^1$ and $Q^2$ both represent phosphorus;
K represents hydrogen or unsubstituted $C_1$-$C_6$ alkyl, particularly hydrogen;
D and E together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(5) $(CR^7R^8R^9)$ and $(CR^{10}R^{11}R^{12})$ together with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
A and B are the same and represent —$CH_2$—;
K, D and E are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(6) $(CR^7R^8R^9)$ and $(CR^{10}R^{11}R^{12})$ together with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
K represents —$CH_2$-$Q^3(X^5)X^6$ wherein $X^5$ and $X^6$ together with $Q^3$ to which they are attached represents 2-phospha-adamantyl;
A and B are the same and represent —$CH_2$—;
$Q^1$, $Q^2$ and $Q^3$ each represent phosphorus;
D and E are the same and represent hydrogen or unsubstituted $C_1$-$C_6$ alkyl, particularly hydrogen;
M represents Fe;
n=1 and $L_1$ represents cyclopentadienyl, particularly unsubstituted-cyclopentadienyl, and m=0.

(7) $(CR^7R^8R^9)$ and $(CR^{10}R^{11}R^{12})$ together with $Q^2$ to which they are attached represent 2-phospha-adamantyl;
$(CR^4R^5R^6)$ and $(CR^1R^2R^3)$ together with $Q^1$ to which they are attached represent 2-phospha-adamantyl;
K represents —$CH_2$-$Q^3(X^5)$ $X^6$ wherein $X^5$ and $X^6$ together with $Q^3$ to which they are attached represents 2-phospha-adamantyl;
$A_1$ and $A_2$ are the same and represent —$CH_2$—;
$Q^1$, $Q^2$ and $Q^3$ each represent phosphorus;
D and E together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

Suitably, the process of the invention may be used to catalyze the hydroformylation of an ethylenically unsaturated compound in the presence of carbon monoxide and hydrogen, i.e. the process of the invention may catalyze the conversion of an ethylenically unsaturated compound to the corresponding aldehyde. Conveniently, the process of the invention will show an increased selectivity to the linear aldehyde product, compared to the branched aldehyde product, in comparison with similar processes but where the chlorine moiety is not present. Preferably, the ratio of linear:branched product obtained from the hydroformylation process is greater than when using comparable catalyst systems/solvents but wherein a chlorine moiety is not present i.e. the ratio is biased towards the linear product, more preferably the linear: branched ratio is greater than 1:1, more preferably is greater than 1.25:1, even more preferably is greater than 1.5:1, yet more preferably is greater than 2:1, most preferably is greater than 3:1.

Conveniently, the process of the invention may utilize highly stable compounds under typical hydroformylation reaction conditions such that they require little or no replenishment. Conveniently, the process of the invention may have an increased rate of the hydroformylation reaction of an ethylenically unsaturated compound compared to known processes. Conveniently, the process of the invention may promote high conversion rates of the ethylenically unsaturated compound, thereby yielding the desired product in high yield with little or no impurities. Consequently, the commercial viability of the hydroformylation process, such as the hydroformylation of an ethylenically unsaturated compound, may be increased by employing the process of the invention.

The following definitions apply to all sets of embodiments noted hereinbefore and where applicable, unless otherwise stated.

The term "Ar" or "aryl" when used herein, and unless otherwise indicated, includes five-to-ten membered, preferably six-to-ten-membered carbocyclic aromatic or pseudo aromatic groups, such as phenyl, ferrocenyl and naphthyl, preferably phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined below).

Suitably, when Ar or aryl is cyclopentadienyl and when D and E together with the carbon atoms of the cyclopentadienyl ring to which they are attached form a phenyl ring, the metal M or cation thereof is attached to an indenyl ring system. In a preferred embodiment Ar represents phenyl or naphthyl, more preferably, phenyl and in either case they may be optionally substituted as set out in the previous paragraph.

The term "Het", when used herein, includes four-to-twelve-membered, preferably four-to-ten-membered ring systems, which rings contain one or more heteroatoms selected from nitrogen, oxygen, sulfur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and, piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulfur atoms, or by silano or dialkylsilicon groups.

Lower alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulfur atoms, or by silano or dialkylsilicon groups, and/or be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het wherein $R^{19}$ to $R^{27}$ each independently represent hydrogen, aryl or lower alkyl.

Similarly, the term "lower alkylene" which A, B and J (when present) represent in a compound of formula (I), and which R represents in a compound of formula (Ia), when used herein, includes $C_1$ to $C_{10}$ groups which can be bonded at two places on the group and is otherwise defined in the same way as "lower alkyl".

Halo groups with which the above-mentioned groups may be substituted or terminated include fluoro, chloro, bromo and iodo groups.

Where a compound of the formula (I) or (Ia) contains an alkenyl group, cis (E) and trans (Z) isomerism may also occur. The present invention includes the individual stereoisomers of the compounds of formula (I) and, where appropriate, the individual tautomeric forms thereof, together with mixtures thereof. Separation of diastereoisomers or cis and trans isomers may be achieved by conventional techniques, e.g. by fractional crystallization, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallization of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula (I), or compounds of formula (Ia), i.e. (b) above, may function as ligands that coordinate with the Group VIII metal or compound thereof, i.e. (a) above, to form the compounds for use in the invention. Typically, the Group VIII metal or compound thereof, i.e. (a) above, coordinates to the one or more phosphorous, arsenic and/or antimony atoms of the compound of formula (I).

The details and embodiments which follow hereinafter apply to all sets of embodiments noted hereinbefore.

As noted hereinbefore, the present invention provides a process for the hydroformylation of an ethylenically unsaturated compound comprising contacting an ethylenically unsaturated compound with carbon monoxide and hydrogen in the presence of a catalyst system and solvent as defined in the present invention.

Suitably, the hydroformylation reaction is carried out at a temperature of between 20° C. and 180° C., more preferably 35° C. and 165° C., yet more preferably 50° C. to 150° C., even more preferably 55° C. to 115° C., most preferably 60° C. to 95° C., for example at about 80° C., and under a partial pressure of carbon monoxide/hydrogen in the range of 1 to 700 bar, preferably 1 to 600 bar, more preferably 1 to 300 bar, even more preferably 15 to 100 bar, yet even more preferably 20 to 45 bar, most preferably 25 to 40 bar, for example at about 30 bar.

Suitably, the ethylenically unsaturated compound may include more than one carbon-carbon double bond, wherein the double bonds are conjugated or non-conjugated.

Preferably, the ethylenically unsaturated compound has 1 to 3 carbon-carbon double bonds per molecule, particularly only 1 or 2 carbon-carbon double bonds per molecule, generally only 1 carbon-carbon double bond per molecule.

In the process according to the present invention, the carbon monoxide and hydrogen may be used either in pure form or diluted with an inert gas such as nitrogen, carbon dioxide or a noble gas such as argon.

The amount of the catalyst of the invention used in the hydroformylation process of the ethylenically unsaturated compound is not critical. Good results may be obtained when, preferably, the amount of Group VIII metal is in the range $10^{-7}$ to $10^{-1}$ moles per mole of ethylenically unsaturated compound, more preferably, $10^{-6}$ to $10^{-2}$ moles, most preferably $10^{-5}$ to $10^{-2}$ moles per mole of ethylenically unsaturated compound. Preferably, the amount of bidentate compound of formula (I), or of formula (Ia), to unsaturated compound is in the range $10^{-7}$ to $10^{-1}$ more preferably, $10^{-6}$ to $10^{-2}$, most preferably, $10^{-5}$ to $10^{-2}$ moles per mole of ethylenically unsaturated compound.

The catalyst compounds of the present invention may act as a "heterogeneous" catalyst or a "homogeneous" catalyst.

By the term "homogeneous" catalyst we mean a catalyst, i.e. a compound of the invention, which is not supported but is simply admixed or formed in-situ with the reactants of the hydroformylation reaction (e.g. the ethylenically unsaturated compound, hydrogen and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the hydroformylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalized silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 µm. More preferably, the surface area is in the range of from 50 to 500 $m^2/g$, the pore volume, is in the range of from 0.5 to 2.5 cc/g and the average particle size is in the range of from 20 to 200 µm. Most desirably, the surface area is in the range of from 100 to 400 $m^2/g$, the pore volume is in the range of from 0.8 to 2.0 cc/g and the average particle size is in the range of from 30 to 100 µm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or rigid and the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compounds from the insoluble support.

The compounds of the invention may be fixed to the surface of the insoluble support by promoting reaction of a functional group present in the compound of formula (I), for example a substituent K, D, Z and E of the aryl moiety, or formula (Ia), with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depends upon the nature of the substituents(s) of the compound and the groups of the support. For example, reagents such as carbodiimides, 1,1'-carbonyldiimidazole, and processes such as the use of mixed anhydrides, reductive amination may be employed.

According to a further aspect, the present invention provides the use of the process of the invention wherein the catalyst is attached to a support.

Particularly preferred is when the organic groups $R^1$, $R^2$, $R^3$, $R^4$, $R^5$, $R^6$, $R^7$, $R^8$, $R^9$, $R^{10}$, $R^{11}$ and $R^{12}$ when associated with their respective carbon atom form composite groups which are at least as sterically hindering as t-butyl. Steric hindrance in this context is as discussed at page 14 et seq of "Homogenous Transition Metal Catalysis—A Gentle Art", by C Masters, published by Chapman and Hall 1981.

These steric groups may be cyclic, part-cyclic or acyclic, preferably acyclic. When cyclic or part cyclic, the group may be substituted or unsubstituted or be saturated or unsaturated. The cyclic or part cyclic groups may contain; including the tertiary carbon atom, from $C_4$-$C_{30}$, more preferably $C_6$-$C_{20}$, most preferably $C_{10}$-$C_{15}$ carbon atoms in the cyclic structure. The cyclic structure may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulphur atoms, or by silano or dialkylsilicon groups.

In certain embodiments, as noted above, the bridging group Ar is an aryl moiety, e.g. a phenyl group, which may be optionally substituted, provided that the two phosphorus atoms are linked to adjacent carbon atoms, e.g. at the 1 and 2 positions on the phenyl group. Furthermore, the aryl moiety may be a fused polycyclic group, e.g. naphthalene, biphenylene or indene. However, preferably the aryl moiety is phenyl or napthalene, more preferably phenyl.

Examples of suitable specific but non-limiting examples of bidentate ligands are 1,2-bis-(di-tert-butylphosphinomethyl)benzene, 1,2-bis-(di-tert-pentylphosphinomethyl)benzene, 1,2-bis-(di-tert-butylphosphinomethyl)naphthalene, 1,2 bis(diadamantylphosphinomethyl)benzene, 1,2 bis(di-3,5-dimethyladamantylphosphinomethyl)benzene, 1,2 bis(di-5-tert-butyladamantaylphosphinomethyl)benzene, 1,2 bis(1-adamantyl tert-butyl-phosphinomethyl)benzene, 1,2 bis(di-1-diamantanephosphinomethyl)benzene, 1-[(diadamantylphosphinomethyl)-2-(di-tert-butylphosphinomethyl)]benzene, 1-(di-tert-butylphosphinomethyl)-2-(dicongressylphosphinomethyl)benzene, 1-(di-tert-butylphosphinomethyl)-2-(phospha-adamantylphosphinomethyl)benzene, 1-(diadamantylphosphinomethyl)-2-(phospha-adamantylphosphinomethyl)benzene, 1-(tert-butyladamantyl)-2-(di-adamantyl)-(phosphinomethyl)benzene and 1-[(P-(2,2,6,6,-tetra-methylphosphinan-4-one)phosphinomethyl)]-2-(phospha-adamantylphosphinomethyl)benzene, 1,2-bis-(ditertbutylphosphinomethyl)ferrocene, 1,2-bis-(ditertbutylphosphinomethyl)ferrocene, 1,2,3-tris-(ditertbutylphosphinomethyl)ferrocene, 1,2-bis-(dicyclohexylphosphinomethyl)ferrocene, 1,2-bis-(di-iso-butylphosphinomethyl)ferrocene, 1,2-bis-(dicyclopentylphosphinomethyl)ferrocene, 1,2-bis-(diethylphosphinomethyl)ferrocene, 1,2-bis(diisopropylphosphinomethyl)ferrocene, 1,2-bis-(dimethylphosphinomethyl)ferrocene, 1,2-bis-(di-(1,3,5,7-tetramethyl-6,9,10-trioxa-2-phospha-adamantylmethyl))ferrocene, 1,2-bis-α,α-(P-(2,2,6,6,-tetramethylphosphinan-4-one)) dimethylferrocene, and 1,2-bis-(di-1,3,5,7-tetramethyl-6,9, 10-trioxa-2-phospha-adamantylmethyl))benzene, preferably selected from bis (di-t-butyl phosphino)-o-xylene (also known as 1,2 bis (di-t-butylphosphinomethyl)benzene); 1,2 bis (diadamantylphosphinomethyl)benzene; 1,2 bis (diadamantylphosphinomethyl)naphthalene; 1,2 bis(di-t-pentylphosphino)-o-xylene (also known as 1,2 bis(di-t-pentylphosphinomethyl)benzene); and bis 1,2 (di-t-butyl phosphinomethyl)naphthalene. Additionally, the bidentate phosphine may be bonded to a suitable polymeric substrate via at least one of the bridging group Ar, the linking group A or the linking group B, e.g. bis(di-t-butyl phosphino)-o-xylene may be bonded via the xylene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group VIII metal present is from 1 to 50, e.g. from 1 to 10, and particularly from 1 to 5, mol per mol of metal. More preferably, the mol:mol range of compounds of formula (I) or (Ia), preferably formula (I), to, Group VIII metal is in the range of 1:1 to 3:1, most preferably in the range of 1:1 to 1.25:1. Conveniently, the possibility of applying these low molar ratios is advantageous, as it avoids the use of an excess of the compound of formula (I) or (Ia), preferably formula (I), and hence minimizes the consumption of these usually quite expensive compounds. Suitably, the catalysts of the process of the invention are prepared in a separate step preceding their use in-situ in the hydroformylation reaction of an ethylenically unsaturated compound.

The carbon monoxide and hydrogen may be used in the presence of other gases which are inert in the reaction. Examples of such gases include nitrogen, carbon dioxide and the noble gases such as argon.

Suitable Group VIII metals (otherwise known as Group VIIIB metals) or a compound thereof which may be combined with a compound of formula (I) include cobalt, nickel, palladium, rhodium, ruthenium and platinum. Preferably, (a) is rhodium or a compound thereof. Suitable compounds of such Group VIII metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. A further alternative includes halo salts. Other sources which may provide suitable anions include the optionally halogenated tetraphenyl borate derivatives, e.g. perfluorotetraphenyl borate. Moreover, metal complexes, particularly those with labile ligands, may be used. Of course, the process of the invention requires a catalyst system obtainable by, combining a Group VIII metal or a compound thereof and a bidentate phosphine, with the presence of a chlorine moiety in at least one of the Group VIII metal compound or the solvent, and therefore should the solvent not contain a chlorine moiety, the Group VIII metal compound must contain a chlorine moiety, and the foregoing is to be read accordingly. Of course, should the chlorine moiety be present in the solvent, then the moiety can be present in any part of the solvent system, e.g. wherein the solvent system may comprise a solvent and, for example, a chlorine moiety source, preferably the chlorine moiety is present within the chemical structure of the solvent molecules themselves, e.g. in chlorohydrocarbon solvents, chlorofluorocarbon solvents, and the like.

The catalyst system of the present invention is preferably constituted in the liquid phase which may be formed by one or more of the reactants or by the use of a suitable solvent. Clearly, in the former case, the references to solvent in the present invention should be construed accordingly and the chlorine moiety must, in such cases, be present in the Group VIII metal compound.

The choice of solvent is not critical, aside from the fact that according to the invention, it must comprise a chlorine moiety if the Group VIII metal compound does not. Naturally, the solvent chosen should not be detrimental to either the catalyst system, reactants or products. Moreover, the solvent can be a mixture of reactants, such as the ethylenically unsaturated compound, the product and/or any by-products, and the higher-boiling products of secondary reactions thereof, e.g. aldol condensation products. Moreover, more than one solvent can be present, e.g. a mixture of solvents.

Suitable solvents, when present, include saturated hydrocarbons such as kerosene, mineral oil or cyclohexane, ethers such as diphenyl ether, methyl phenyl ether, diethylether, diisopropylether, tetrahydrofuran or a polyglycol, ketones such as acetone, methyl ethyl ketone, methyl butyl ketone and cyclohexanone, nitriles such as methylglutaronitrile, valeironitrile, and benzonitrile, aromatics, including halo variants, such as toluene, benzene and xylene, esters such as methylacetate, methylvalerate and caprolactone, dimethylformamide, and sulfones such as tetramethylenesulfone, and variants of any of the aforesaid comprising at least one chlorine moiety.

Other suitable solvents include aromatic compounds such as toluene (as noted above), hydrocarbons or mixtures of hydrocarbons. It is, also possible to use water, and alcohols such as methanol, ethanol, n-propanol, isopropanol, n-butanol and isobutanol. Variants of the aforesaid comprising at least one chlorine moiety are also suitable.

As noted hereinbefore, a chlorine moiety is present in at least one of the Group VIII metal compound or solvent of the process of the invention. Thus, suitably, the Group VIII metal compound is as defined hereinbefore and comprising a chlorine moiety. Specific examples of suitable Group VIII compounds include rhodium complexes (both those with and those without at least one chlorine moiety) and are such as $[RhCl(CO)_2]_2$, $[RhCl(Cod)_2]_2$, (wherein "Cod" represents "1,5-cyclooctadiene"), $RhCl_3.xH_2O$, $[Rh(CO)_2(acac)]_2$ (wherein "acac" represents "acetylacetonate"), $[Rh(acetate)_2]_2$, $[RhCl(Norbornadiene)]_2$, $Rh_2(OAc)_4$, $[RhCl(Cyclooctene)_2]_2$, Chloro(1,5-hexadiene)-rhodium(I)dimer, Bis(1,5-cyclooctadiene)-rhodium(I)tetrafluoroborate hydrate, μ-dichlorotetraethylene-dirhodium, (bicyclo[2,2,1] hepta-2-5-diene)chlororhodium(I)dimer, (1,5-cyclooctadiene)(2,4-pentanedionato)rhodium(I), (bicyclo[2,2,1]hepta-2-5-diene)-(2,4-pentanedionato)rhodium(I), rhodium(III) acetylacetonate, (bicyclo[2,2,1]hepta-2-5-diene) chlororhodium(I)dimer, more especially $[RhCl(CO)_2]_2$, $[RhCl(Cod)_2]_2$, $RhCl_3.xH_2O$, $[Rh(CO)_2(acac)]_2$, $[Rh(acetate)_2]_2$ $[RhCl(Norbornadiene)]_2$ $[RhCl(Cyclooctene)_2]_2$, Chloro(1,5-hexadiene)-rhodium(I)dimer, most especially

[RhCl(CO)$_2$]$_2$, [RhCl(Cod)$_2$]$_2$, RhCl$_3$.xH$_2$O, [Rh(CO)$_2$(acac)]$_2$, [Rh(acetate)$_2$]$_2$. Thus, where the rhodium complexes are to comprise at least one chlorine moiety, suitable complexes include [RhCl(CO)$_2$]$_2$, [RhCl(Cod)$_2$]$_2$, RhCl$_3$.xH$_2$O, [RhCl(Norborn-adiene)]$_2$, [RhCl(Cyclooctene)$_2$]$_2$, Chloro(1,5-hexadiene)-rhodium(I)dimer, μ-dichlorotetraethylene-dirhodium, (bicyclo[2,2,1]hepta-2-5-diene)chlororhodium(I)dimer, more especially [RhCl(CO)$_2$]$_2$, [RhCl(Cod)$_2$]$_2$, RhCl$_3$.xH$_2$O, [RhCl(Norbornadiene)]$_2$, [RhCl(Cyclooctene)$_2$]$_2$, Chloro(1,5-hexadiene)-rhodium(I)dimer, most especially [RhCl(CO)$_2$]$_2$, [RhCl(Cod)$_2$]$_2$, RhCl$_3$.xH$_2$O. Moreover, suitably, the solvent of the process of the invention is as defined hereinbefore and comprising a chlorine moiety. Specific examples of such solvents comprising at least one chloro moiety include dichloromethane, chlorobenzene, o-dichlorobenzene, m-chlorobenzene, carbon tetrachloride, trichloroethanes, dichloroethanes, chlorofluorocarbons (CFC's), tetrachloroethanes, tetrachloroethene, more especially dichloromethane. Even more preferably, both the Group VIII metal compound and the solvent contain a chlorine moiety.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity and linearity. A further advantage is that the other components which contain the catalyst system may be recycled and/or reused in further reactions with minimal supplementation of fresh catalyst.

Preferably, the hydroformylation is carried out at a temperature of between 20° C. and 180° C., more preferably 35° C. and 165° C., yet more preferably 50° C. to 150° C., even more preferably 55° C. to 115° C., most preferably 60° C. to 95° C., for example at about 80° C. Advantageously, the hydroformylation can be carried out, at moderate temperatures. It is particularly advantageous to be able to carry out the hydroformylation reaction at above room temperature.

Suitably, the hydroformylation is carried out at the partial pressure of the reaction gas mixture at the chosen reaction temperature. Generally, the partial pressure is in the range of 1 to 700 bar, preferably 1 to 600 bar, more preferably 1 to 300 bar, even more preferably 15 to 100 bar, yet even more preferably 20 to 45 bar, most preferably 25 to 40 bar, for example at about 30 bar.

However, the partial pressure may be varied from these ranges depending on the activity of the hydroformylation catalyst employed. In the case of catalyst systems of the present invention, for example, reaction would also proceed in a low-pressure region, for example in the range 1 to 100 bar.

The reaction may be carried out on any ethylenically unsaturated compound including ethylene although there is no linearity advantage as such with ethylene. Preferably, the reaction is therefore suitable for $C_3$-$C_{20}$ ethylenically unsaturated compounds, more preferably, $C_3$-$C_{18}$, most preferably $C_3$-$C_{12}$ compounds.

The process may be carried out on ethylenically unsaturated compounds having 2 or more carbon atoms such as $C_2$-$C_{20}$ atoms or $C_3$-$C_{20}$ atoms or $C_4$-$C_{20}$ atoms. The alternative upper range of carbon atoms in such compounds may be taken as $C_{18}$ or $C_{15}$ or $C_{12}$ in increasing order of preference. The alternative lower range of carbon atoms in any of the aforesaid ranges of ethylenically unsaturated compounds may be $C_3$, $C_4$, $C_5$ or $C_6$. The ethylenically unsaturated compound is, preferably, an alkene having 1, 2 or 3 or more carbon-carbon double bonds per molecule.

Any such alkene can be substituted or non-substituted. Suitable substituents include $C_{1-8}$ alkyl and $C_{1-22}$ aryl groups. Unless otherwise specified, the ethylenically unsaturated compound may, when there are sufficient number of carbon atoms, be linear or branched, be substituted, be cyclic, acyclic or part cyclic/acyclic, and/or be optionally substituted or terminated by one or more substituents selected from lower alkyl, aryl, alkylaryl, Het, alkylHet, halo, OR$^{19}$, OC(O)R$^{20}$, C(O)R$^{21}$, C(O)OR$^{22}$, NR$^{23}$R$^{24}$, C(O)NR$^{25}$R$^{26}$, NO$_2$, CN, SR$^{27}$ wherein R$^{19}$ to R$^{27}$ each independently represent hydrogen or lower alkyl. Olefins thus substituted include styrene and alkyl esters of unsaturated carboxylic acids, such as methacrylate. Suitably, the ethylenically unsaturated compound may exhibit cis (E) and trans (Z) isomerism.

Examples of suitable ethylenically unsaturated compounds may be independently selected from ethene, propene, 1-butene, 2-butene, isobutene, 1-pentene, 2-pentene, 3-pentene and branched isomers thereof, 1-hexene and its isomers, 1-heptene and its isomers, 1-octene and its isomers, 1-nonene and its isomers, 1-decene and its isomers, the $C_{11}$-$C_{20}$ alkenes and their known isomers, 3-pentenenitrile, methyl-3-penteneoate, 1,3 butadiene, 1,3-pentadiene, 1,3 hexadiene, 1,3 cyclohexadiene, 2,4-leptadiene, and 2-methyl 1.3 butadiene. Preferably, the ethylenically unsaturated compound is a $C_2$-$C_{20}$ alkene, more preferably a $C_3$-$C_{20}$ alkene with a carbon-carbon double bond in the 1-position, most preferably a $C_3$-$C_{12}$ or $C_6$-$C_{12}$ alkene with a carbon-carbon double bond in the 1-position.

The use of stabilizing compounds with the catalyst system may also be beneficial in improving recovery of metal which has been lost from the catalyst system. When the catalyst system is utilized in a liquid reaction medium such stabilizing compounds may assist recovery of the Group VIIIB metal.

Preferably, therefore, the catalyst system includes in a liquid reaction medium a polymeric dispersant dissolved in a liquid carrier, said polymeric dispersant being capable of stabilizing a colloidal suspension of particles of the Group VIII metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilizing a colloidal suspension of particles of said Group VIII metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed Group VIII metal particles are stabilized against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimized then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilize the colloidal suspension of said Group VIII metal or metal compound.

By substantially stabilize is meant that the precipitation of the Group VIII metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid).

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed Group VIII metal may be recovered from the liquid stream-removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

In a further aspect the present invention provides a catalyst system, preferably wherein said system is for use in a process for the hydroformylation of ethylenically unsaturated compounds and which process comprises reacting said ethylenically unsaturated compound with carbon monoxide and hydrogen, in the presence of said system, the catalyst system obtainable by combining:
 a) a Group VIII metal compound as described or defined hereinbefore; and
 b) a bidentate phosphine as described or defined hereinbefore, and wherein the catalyst system is characterised in that a chlorine moiety is present in at least said Group VIII metal compound.

In a yet further aspect the present invention provides a hydroformylation reaction catalyst system for the catalysis of ethylenically unsaturated compounds with carbon monoxide and hydrogen in the presence of said system, the catalyst system obtainable by combining:
 a) a Group VIII metal compound as described or defined hereinbefore; and
 b) a bidentate phosphine as described or defined hereinbefore, and wherein the catalyst system is characterised in that a chlorine, moiety is present in at least said Group VIII metal compound.

In a still further aspect the present invention provides a reaction medium comprising a catalyst system and a solvent, preferably wherein said medium is for use in a process for the hydroformylation of ethylenically unsaturated compounds and which process comprises reacting said ethylenically unsaturated compound with carbon monoxide and hydrogen, in the presence of said system and said solvent, wherein said solvent is as described or defined hereinbefore, the catalyst system obtainable by combining:
 a) a metal of Group VIII or a compound thereof as described or defined hereinbefore; and
 b) a bidentate phosphine as described or defined hereinbefore, and wherein the reaction medium is characterised in that a chlorine moiety is present in at least one of the said Group VIII metal compound or said solvent, including the possibility of being present in both.

In a still yet further aspect the present invention provides a hydroformylation reaction medium, wherein said medium comprises a catalyst system and a solvent, preferably wherein said system is for use in a process for the hydroformylation of ethylenically unsaturated compounds and which process comprises reacting said ethylenically unsaturated compound with carbon monoxide and hydrogen, in the presence of said system and said solvent, wherein said solvent is as described or defined hereinbefore, the catalyst system obtainable by combining:
 a) a metal of Group VIII or a compound thereof as described or defined hereinbefore; and
 b) a bidentate phosphine as described or defined hereinbefore, and wherein the reaction medium is characterised in that a chlorine moiety is present in at least one of the said Group VIII metal compound or said solvent, including the possibility of being present in both.

In a still yet further aspect of the present invention there is provided the use of a catalyst system as defined or described hereinbefore for the hydroformylation of ethylenically unsaturated compounds, said use comprising the step of reacting said ethylenically unsaturated compound with carbon monoxide and hydrogen, in the presence of said catalyst system.

In a still yet further aspect of the present invention there is provided the use of a reaction medium as defined or described hereinbefore for the hydroformylation of ethylenically unsaturated compounds, said use comprising the step of reacting said ethylenically unsaturated compound with carbon monoxide and hydrogen, in the presence of said reaction medium.

In a still further aspect of the present invention there is provided a process for preparing a catalyst system or a reaction medium as defined or described hereinbefore, comprising combining (a) a metal of Group VIII or a compound thereof as described or defined hereinbefore, and (b) a bidentate phosphine as described or defined hereinbefore.

Features and embodiments of the first aspect of the invention are equally applicable to any or all of the various aspects of the present invention as set out herein, unless such features/embodiments are incompatible with the particular aspect, or are mutually exclusive.

The following non-limiting and purely illustrative examples further illustrate the present invention.

All syntheses were carried out in a vacuum-argon Schlenk line using dried and degassed Schlenk glassware.

1-octene and 1-hexene (both from Aldrich) were purified by distillation and degassed by bubbling with argon. Toluene was dried by distillation from sodium diphenyl ketal. THF (tetrahydrofuran) was dried by distillation with sodium and benzophenone. DCM (dichloromethane) was dried by distillation with calcium hydride.

$[RhCl(CO)_2]_2$, $Rh_2(OAc)_4$, and $RhCl_3 \cdot xH_2O$ (Strem) were stored in a glove box due to their air-sensitive nature. 1,2-bis(di-tertbutylphosphinomethyl)benzene was also stored and handled in a glove box due to its air-sensitive nature.

1,2-bis(di-tertbutylphosphinomethyl)benzene is available from Strem Chemicals (Catalog 19 No. 15-0072, CAS No. 121954-50-5) or can, as in these examples, be prepared as per example 18 of WO-A-99/47528, PCT/GB99/00797, details of the preparation being incorporated by reference thereto.

The preparation details of 1,2-bis-(diadamantylphosphinomethyl)benzene and other adamantyl-based ligands are given in the Applicant's published application, WO-A-04/014552, PCT/GB03/003419, herein incorporated by reference, particularly for such preparation details.

The preparation details of 1,2-bis-(di-t-butylphosphinomethyl)ferrocene and other ferrocene-based ligands are given in the Applicant's published application, WO-A-04/024322, PCT/GB03/003936, herein incorporated by reference, particularly for such preparation details.

The catalytic solutions were made up as follows.

For catalytic systems having $[RhCl(CO)_2]_2$ as rhodium precursor, 9 mg (0.023 mmol) of $[RhCl(CO)_2]_2$ and 20 mg (0.046 mmol) of 1,2-bis(di-tertbutylphosphinomethyl)benzene were added to a Schlenk tube in a glove box. The corresponding solvent (typically 10 ml) was then added with a syringe. When all the solids were dissolved, 1-octene or 1-hexene (2 ml), the substrate for hydroformylation, was added to the solution.

The autoclaves used for these examples were 250 ml hastelloy autoclaves. After being dried in an oven, the autoclave was flushed three-times with argon. Once it was degassed, the solution was transferred via canula. Then it was pressured with 30 bar of synthesis gas and heated to 80° C. for 3 hrs, after which it was cooled in air and then vented. The solutions obtained were analyzed with GC-MS.

The catalytic systems in which either $Rh_2(OAc)_4$ or $RhCl_3$ were used as rhodium precursors, were prepared following the same procedure as that outlined above.

The percentage conversion is an expression of the amount of substrate converted by the reaction.

The selectivity is a measure of the selectivity to the particular hydroformylated product.

l:b is a representation of the linear:branched ratio of the hydroformylated products.

EXAMPLE 1

Hydroformylation of 1-hexane: Chlorine Moiety Present in Rhodium Precursor 9.0 mg (0.00383 mol/liter) of $[RhCl(CO)_2]_2$ was added to 18 mg (0.00383 mol/liter) of the bidentate phosphine ligand, 1,2-bis(di-tertbutylphosphinomethyl)benzene. 10 ml of toluene was then added to the mixture. 2.0 ml (16.0 mmol) of 1-hexene was then added and hydroformylation was performed for 3 hrs by the addition, at 80° C., of a 1:1 mixture of $CO:H_2$ at a pressure of 30 bar.

It was found that after 3 hrs under these conditions, there was 100% conversion of 1-hexene to the aldehyde product, with 84% selectivity to linear heptanal over the branched product, an l:b ratio of 5.25:1.

COMPARATIVE EXAMPLE 1

Hydroformylation of 1-hexene: Chlorine Moiety not Present 10 mg (0.00383 mol/liter) of $[Rh(OAc)_2]_2$ was added to 40 mg (0.00846 mol/liter) of the bidentate phosphine ligand, 1,2-bis(di-tertbutylphosphinomethyl)benzene. 10 ml of toluene was then added to the mixture. 2.0 ml (16.0 mmol) of 1-hexene was then added and hydroformylation was performed for 3 hrs by the addition, at 80° C., of a 1:1 mixture of $CO:H_2$ at a pressure of 30 bar.

It was found that after 3 hrs under these conditions, there was 100% conversion of 1-hexene to the aldehyde product; with 55% selectivity to linear heptanal over the branched product, an l:b ratio of only 1.22:1.

Comparative Example 1 and Example 1 clearly show the increase in selectivity towards the linear product over the branched product, from the hydroformylation of 1-hexene, when chlorine moiety is present in the rhodium compound precursor to the catalyst system compared with when the chlorine moiety is not present.

EXAMPLE 2

Hydroformylation of Allyl Alcohol: Chlorine Moiety Present in Rhodium Precursor 9.0 mg (0.00383 mol/liter) of $[RhCl(Cod)_2]_2$ was added to 18.0° mg (0.00383 mol/liter) of the bidentate phosphine ligand, 1,2-bis(di-tertbutylphosphinomethyl)benzene. 10 ml of toluene was then added to the mixture. 2.0 ml (29.0 mmol) of allyl alcohol was then added and hydroformylation was performed for 3 hrs by the addition, at 80° C., of a 1:1 mixture of $CO:H_2$ at a pressure of 30 bar, and in the presence of 0.072 mmol of NaOAc.

It was found that after 3 hrs under these conditions, there was 86.6% conversion of allyl alcohol, with 73.8% selectivity to hydroxytetrahydrofuran, 12.9% to hydroxymethyl-propionaldehyde. These two products were then hydrogenated to give, respectively, 1,4-butanediol and 2-methyl-1,3-propanediol. The l:b ratio in this case was 5.72:1.

EXAMPLE 3

Hydroformylation of Allyl Alcohol: Chlorine Moiety Present in Solvent

Example 2 was repeated but in this case, the rhodium compound was $[Rh(OAc)_2]_2$ and the solvent used was dichloromethane.

In this case, there was 100% conversion of allyl alcohol, with 75% selectivity to hydroxytetrahydrofuran, 17% hydroxymethylpropionaldehyde, giving hydrogenated products in the l:b ratio 4.41:1.

Examples 2 and 3 show the relatively high selectivity towards the linear as opposed to the branched product, from the hydroformylation of allyl alcohol, when chlorine moiety is present in the rhodium compound precursor to the catalyst system (Example 2) or in the solvent (Example 3).

EXAMPLE 4

Hydroformylation of 1-octene: Chlorine Moiety Present in Solvent 5.0 mg (0.0016 mol/liter) of $[Rh(acac)(CO)_2]_2$ was added to 18.0 mg (0.00383 mol/liter) of the biphosphine ligand, 1,2-bis(di-tertbutylphosphinomethyl)benzene. 10 ml of dichloromethane was then added to the mixture. 2.5 ml (16 mmol) of 1-octene was then added and hydroformylation was performed for 3 hrs by the addition, at 80° C., of a 1:1 mixture of $CO:H_2$ at a pressure of 30 bar.

It was found that after 3 hrs under these conditions, there was 29% conversion to the aldehyde product, with 80% selectivity to linear nonanal over the branched product, an l:b ratio of 4:1.

EXAMPLE 5

Hydroformylation of 1-octene: Chlorine Moiety Present in Rhodium Precursor and in Solvent Details were as in Example 4 above, except 9.0 mg (0.00383 mol/liter) of $[RhCl(CO)_2]_2$ was used as the rhodium precursor.

Once again, it was found that there was 29% conversion to the aldehyde product, with 80% selectivity to linear nonanal over the branched product, an l:b ratio of 4:1.

EXAMPLE 6

Hydroformylation of 1-octene: Chlorine Moiety Present in Rhodium Precursor

Details were as in Example 5 above, except 10 ml of OctMiMTfN, 1-octyl-3-methylimidazolium bis-trifluoromethylsulphonamide, a non-chlorine containing solvent, was used as the solvent.

In this case, it was found that there was 10% conversion to the aldehyde product, with 80% selectivity to linear nonanal over the branched product, an l:b ratio of 4:1.

EXAMPLE 7

Hydroformylation of 1-octene: Chlorine Moiety Present in Rhodium Precursor

Details were as in Example 5 above, except 10 ml of toluene was used as the solvent.

In this case, it was found that there was 11% conversion to the aldehyde product, with 100% selectivity to linear nonanal.

COMPARATIVE EXAMPLE 2

Hydroformylation of 1-octene: Chlorine Moiety not Present

Details were as in Example 4 above, except 10 ml of toluene was used as the solvent.

In this case, it was found that there was 89% conversion to the aldehyde product, with only 50% selectivity to linear-nonanal, an l:b ratio of 1:1.

Examples 4-7 clearly show the increase in selectivity towards the linear product over the branched product, from the hydroformylation of 1-octene, when chlorine moiety is present in the solvent (Example 4), the rhodium precursor (Examples 6 and 7), or both the solvent and the rhodium precursor (Example 5), compared to Comparative Example 2, where no chlorine moiety is present, either in the rhodium precursor or in the solvent.

Although a few preferred embodiments have been shown and described, it will be appreciated by those skilled in the art that various changes and modifications might be made without departing from the scope of the invention, as defined in the appended claims.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for the hydroformylation of ethylenically unsaturated compounds, which process comprises reacting said ethylenically unsaturated compound with carbon monoxide and hydrogen, in the presence of a catalyst system, the catalyst system obtainable by combining:
a) a Group VIII metal compound; and
b) a bidentate compound of general formula (Ia)

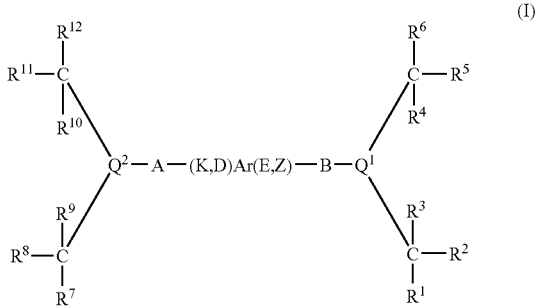
(I)

wherein:
R is a bridging group selected from the group consisting of:
an alkylene group; and
A-Ar—B, in which Ar is an optionally substituted aryl moiety to which A and B are linked on available adjacent carbon atoms, and A and B each independently represent lower alkylene;
$R^1$ to $R^{12}$ each independently represent lower alkyl, aryl or Het;
$Q^1$ and $Q^2$ each independently represent phosphorus, arsenic or antimony, the process characterized in that a chlorine moiety is present in at least said Group VIII metal compound.

2. A process for the hydroformylation of ethylenically unsaturated compounds, which process comprises reacting said ethylenically unsaturated compound with carbon monoxide and hydrogen, in the presence of a catalyst system and a solvent, the catalyst system obtainable by combining:
a) a metal of Group VIII or a compound thereof; and
b) a bidentate compound of general formula (Ia)

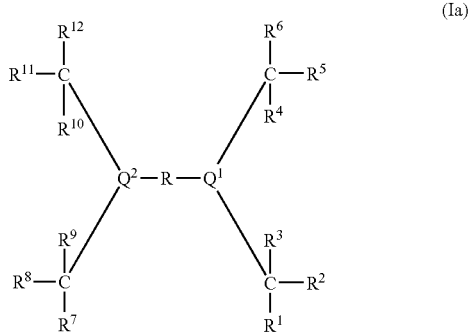
(Ia)

wherein:
R is a bridging group selected from the group consisting of:
an alkylene group; and
A-Ar—B, in which Ar is an optionally substituted aryl moiety to which A and B are linked on available adjacent carbon atoms, and A and B each independently represent lower alkylene;
$R^1$ to $R^{12}$ each independently represent lower alkyl, aryl or Het;

$Q^1$ and $Q^2$ each independently represent phosphorus, arsenic or antimony,
the process characterized in that a chlorine moiety is present in at least one of the said Group VIII metal compound or said solvent.

3. The process as claimed in claim 2, wherein the chlorine moiety is present in both said Group VIII metal compound and said solvent.

4. The process as claimed in claim 1, wherein $R^1$ to $R^{12}$ each independently represent $C_1$ to $C_6$ alkyl, $C_1$ to $C_6$ alkyl phenyl or phenyl.

5. The process as claimed in claim 4, wherein $R^1$ to $R^{12}$ each independently represent methyl, ethyl, n-propyl, iso-propyl, n-butyl, iso-butyl, tert-butyl, pentyl, hexyl and cyclohexyl.

6. The process as claimed in claim 1, wherein $R^1$, $R^4$, $R^7$ and $R^{10}$ each independently represent the same $C_1$-$C_6$ alkyl; $R^2$, $R^5$, $R^8$ and $R^{11}$, each independently represent the same $C_{1-6}$ alkyl; and $R^3$, $R^6$, $R^9$ and $R^{12}$, each independently represent the same $C_{1-6}$ alkyl.

7. The process as claimed in claim 1, wherein $R^1$ to $R^{12}$ each represents the same $C_1$-$C_6$ alkyl group.

8. The process as claimed in claim 7, wherein the said $C_{1-6}$ alkyl group is non-substituted and selected from the list comprising: methyl, ethyl, n-propyl, iso-propyl, n-butyl, iso-butyl, tert-butyl, pentyl, hexyl and cyclohexyl.

9. The process as claimed in claim 8, wherein the said $C_{1-6}$ alkyl group is methyl.

10. The process as claimed in claim 1, wherein $Q^1$ and $Q^2$ represents phosphorus.

11. The process as claimed in claim 1 wherein R is defined as -A-(K,D)Ar(E,Z)—B— and the bidentate compound is of general formula (I)

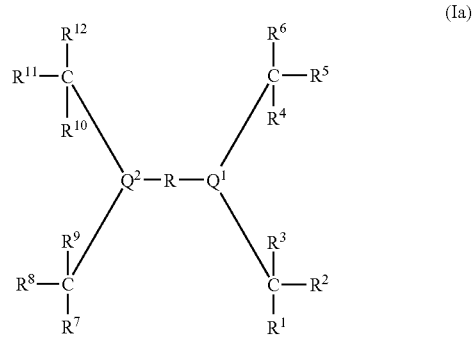
(Ia)

wherein:
Ar is a bridging group comprising an optionally substituted aryl moiety to which A and B are linked on available adjacent carbon atoms;
A and B each independently represent lower alkylene;
K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15}))CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;

$R^1$ to $R^{18}$ each independently represent lower alkyl, aryl, or Het;

$R^{19}$ to $R^{27}$ each independently represent hydrogen, lower alkyl, aryl or Het;

$Q^1$, $Q^2$ and $Q^3$ (when present) each independently represent phosphorous, arsenic or antimony.

12. The process as claimed in claim 11, wherein $R^1$ to $R^{18}$ each independently represent $C_1$ to $C_6$ alkyl, $C_1$ to $C_6$ alkyl phenyl or phenyl.

13. The process as claimed in claim 12, wherein $R^1$ to $R^{18}$ each independently represent methyl, ethyl, n-propyl, iso-propyl, n-butyl, iso-butyl, tert-butyl, pentyl, hexyl and cyclohexyl.

14. The process as claimed in claim 11 wherein $R^1$, $R^4$, $R^7$, $R^{10}$, $R^{13}$ and $R^{16}$ each independently represent the same $C_1$-$C_6$ alkyl; $R^2$, $R^5$, $R^8$, $R^{11}$, $R^{14}$ and $R^{17}$ each independently represent the same $C_{1-6}$ alkyl; and $R^3$, $R^6$, $R^9$, $R^{12}$, $R^{15}$ and $R^{18}$ each independently represent the same $C_{1-6}$ alkyl.

15. The process as claimed in claim 11, wherein $R^1$ to $R^{18}$ each represents the same $C_1$-$C_6$ alkyl group.

16. The process as claimed in claim 15, wherein the said $C_{1-6}$ alkyl group is non-substituted and selected from the list comprising: methyl, ethyl, n-propyl, iso-propyl, n-butyl, iso-butyl, tert-butyl, pentyl, hexyl and cyclohexyl.

17. The process as claimed in claim 16, wherein the said $C_{1-6}$ alkyl group is methyl.

18. The process as claimed in claim 11, wherein $Q^1$, $Q^2$ and $Q^3$ (when present) represents phosphorus.

19. The process as claimed in claim 11, wherein A, B and J (when present) each independently represent $C_1$ to $C_6$ alkylene.

20. The process as claimed in claim 19, wherein each of A, B and J (when present) represent —$CH_2$—.

21. The process as claimed in claim 11, wherein K, D, E and Z each represent hydrogen, phenyl, $C_1$-$C_6$ alkylphenyl or $C_1$-$C_6$ alkyl.

22. The process as claimed in claim 21, wherein K, D, E and Z each represent hydrogen.

23. The process as claimed in claim 11 wherein in formula (I):
A and B each independently represent unsubstituted $C_1$ to $C_6$ alkylene;
K, D, Z and E each independently represent hydrogen, $C_1$-$C_6$ alkyl, phenyl, $C_1$-$C_6$ alkylphenyl or -J-$Q^3$($CR^{13}$($R^{14}$)($R^{15}$))$CR^{16}$($R^{17}$)($R^{18}$) where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl;
$R^1$ to $R^{18}$ each independently represent $C_1$ to $C_6$ alkyl, phenyl or $C_1$ to $C_6$ alkylphenyl.

24. The process as claimed in claim 11 wherein in formula (I):
A and B both represent —$CH_2$— or $C_2H_4$;
K, D, Z and E each independently represent hydrogen, $C_1$-$C_6$ alkyl phenyl or $C_1$-$C_6$ alkyl or -J-$Q^3$($CR^{13}$($R^{14}$)($R^{15}$))$CR^{16}$($R^{17}$)($R^{18}$) where J is the same as A; or two of K, D, E and Z together with the carbon atoms of the aryl ring to which they are attached form an unsubstituted phenyl ring;
$R^1$ to $R^{18}$ each independently represent $C_1$ to $C_6$ alkyl.

25. The process as claimed in claim 24, wherein A and B both represent —$CH_2$—.

26. The process as claimed in claim 11, wherein in formula (I):
each $R^1$ to $R^{12}$ is the same and represents methyl;
A and B are the same and represent —$CH_2$—;
K, D, Z and E are the same and represent hydrogen.

27. The process as claimed in claim 11, wherein the reaction is carried out at a temperature of between 20° C. and 180° C.

28. The process as claimed in claim 27, wherein the temperature is in the range 50° C. to 150° C.

29. The process as claimed in claim 11, wherein the reaction is carried out under a partial pressure of carbon monoxide/hydrogen in the range of 1 to 700 bar.

30. The process as claimed in claim 29, wherein the partial pressure is in the range 1 to 300 bar.

31. The process as claimed in claim 11, wherein said ethylenically unsaturated compound has 1 to 3 carbon-carbon double bonds per molecule.

32. The process as claimed in claim 31, wherein said compound has 1 carbon-carbon double bond per molecule.

33. The process as claimed in claim 11, wherein the amount of bidentate compound of formula (I) to unsaturated compound is in the range $10^{-5}$ to $10^{-2}$ moles per mole of unsaturated compound.

34. The process as claimed in claim 11, wherein said catalyst system further comprises a support.

35. The process as claimed in claim 11, wherein said bidentate compound is a phosphine selected from the group comprising bis (di-t-butyl phosphino)-o-xylene; 1,2 bis (diadamantylphosphinomethyl) benzene; 1,2 bis (diadamantylphosphinomethyl) naphthalene; 1,2 bis (di-t-pentyl phosphino)-o-xylene; and bis 1,2 (di-t-butyl phosphino) naphthalene.

36. The process as claimed in claim 11, wherein the mol:mol range of compounds of formula (I) to Group VIII metal is in the range of 1:1 to 3:1.

37. The process as claimed in claim 36, wherein said mol:mol range is in the range of 1:1 to 1.25:1.

38. The process as claimed in claim 11, wherein the Group VIII metal is selected from the group: cobalt, nickel, palladium, rhodium, ruthenium and platinum.

39. The process as claimed in claim 38, wherein said Group VIII metal is rhodium.

40. The process as claimed in claim 11, wherein said chlorine moiety is present in at least said Group VIII metal compound and said compound is selected from the group comprising: $[RhCl(CO)_2]_2$, $[RhCl(Cod)_2]_2$, $RhCl_3.xH_2O$, [RhCl(Norbornadiene)]$_2$, $[RhCl(Cyclooctene)_2]_2$, Chloro(1,5-hexadiene)-rhodium(I)dimer, μ-dichlorotetraethylenedirhodium, (bicyclo[2,2,1]hepta-2-5-diene)chlororhodium (I)dimer.

41. The process as claimed in claim 11, wherein said chlorine moiety is present in at least said Group VIII metal compound and said compound is selected from the group comprising: $[RhCl(CO)_2]_2$, $[RhCl(Cod)_2]_2$ and $RhCl_3.xH_2O$.

42. The process as claimed in claim 11, wherein said chlorine moiety is present in at least said solvent and said solvent is selected from the group consisting of dichloromethane, chlorobenzene, o-dichlorobenzene, m-chlorobenzene, carbon tetrachloride, trichloroethanes, dichloroethanes, chlorofluorocarbons (CFC's), tetrachloroethanes and tetrachloroethene.

43. The process as claimed in claim 42, wherein said solvent is dichloromethane.

44. The process as claimed in claim 11, wherein said ethylenically unsaturated compound has 2 to 20 carbon atoms.

45. The process as claimed in claim 44, wherein said compound has 5 to 15 carbon atoms.

46. The process as claimed in claim 44, wherein said compound has 6 to 12 carbon atoms.

47. The process as claimed in claim 11, wherein said ethylenically unsaturated compound is selected from the group comprising ethene, propene, 1-butene, 2-butene, isobutene, 1-pentene, 2-pentene, 3-pentene and branched isomers thereof, 1-hexene and its isomers, 1-heptene and its isomers, 1-octene and its isomers, 1-nonene and its isomers, 1-decene and its isomers, the $C_{11}$-$C_{20}$ alkenes and their known isomers, 3-pentenenitrile, methyl-3-penteneoate, 1,3 butadiene, 1,3-pentadiene, 1,3 hexadiene, 1,3 cyclohexadiene, 2,4-leptadiene, and 2-methyl 1,3 butadiene.

48. The process as claimed in claim 11, wherein the said catalyst system further comprises a polymeric dispersant dissolved in a liquid carrier, said polymeric dispersant being capable of stabilizing a colloidal suspension of particles of the Group VIII metal or metal compound of the catalyst system within the said liquid carrier.

49. The process as claimed in claim 48, wherein said polymeric dispersant is selected from the list comprising: polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid).

50. The process as claimed in claim 49, wherein said polymeric dispersant is selected from the list comprising: polyvinylpyrrolidone and polyacrylic acid.

51. The process as claimed in claim 11, wherein the solvent is formed by one or more of the reactants, products or by-products of the process rather than being a separate entity.

52. A process as claimed in claim 11, wherein Ar is defined as including six-to-ten-membered carbocyclic aromatic groups, which groups are optionally substituted with, in addition to K, D, E or Z, one or more substituents selected from aryl, lower alkyl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl.

53. A process as claimed in claim 1 wherein at least one $(CR^xR^yR^z)$group attached to $Q^1$ and/or $Q^2$, i.e. $CR^1R^2R^3$, $CR^4R^5R^6$, $CR^7R^8R^9$, or $CR^{10}R^{11}R^{12}$, may instead be congressyl or adamantyl, or both groups defined above as $(CR^xR^yR^z)$ attached to either or both $Q^1$ and/or $Q^2$, may, together with either $Q^1$ or $Q^2$ as appropriate, instead form an optionally substituted 2-phospha-tricyclo[3.3.1.1{3,7}]decyl group or derivative thereof.

54. A process as claimed in claim 11, wherein Ar is a cyclopentadienyl group, and Z may be represented by -M($L_1$)$_n$ ($L_2$)$_m$ and Z is connected via a metal ligand bond to the cyclopentadienyl group, M represents a Group VIB or VIIIB metal or metal cation thereof; and $L_1$ represents a cyclopentadienyl, indenyl or aryl group each of which groups are optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$ or ferrocenyl;

$L_2$ represents one or more ligands each of which are independently selected from hydrogen, lower alkyl, alkylaryl, halo, CO, $PR^{43}R^{44}R^{45}$ or $NR^{46}R^{47}R^{48}$;

$R^{43}$ to $R^{48}$ each independently represent hydrogen, lower alkyl, aryl or Het;

n=0 or 1;

and m=0 to 5;

provided that when n=1 then m equals 0, and when n equals 0 then m does not equal 0.

55. A process as claimed in claim 1, wherein R represents an alkylene bridging group.

56. A hydroformylation reaction catalyst system comprising a catalyst system and hydrogen for the catalysis of ethylenically unsaturated compounds with carbon monoxide and hydrogen in the presence of said system, the catalyst system obtainable by combining:
   a) a Group VIII metal compound as defined in claim 1; and
   b) a bidentate compound as defined in claim 1, wherein the R bridging group is
      i) an alkylene selected from the group consisting of ethylene and substituted variants thereof, propylene and substituted variants thereof, and butylene and substituted variants thereof; or
      ii) A-Ar—B, in which Ar is an optionally substituted aryl moiety to which A and B are linked on available adjacent carbon atoms, and A and B each independently represent lower alkylene;

and wherein the catalyst system is characterized in that a chlorine moiety is present in at least said Group VIII metal compound.

57. A hydroformylation reaction medium, wherein said medium comprises a catalyst system, a solvent, and hydrogen, wherein said system is for use in a process for the hydroformylation of ethylenically unsaturated compounds and which process comprises reacting said ethylenically unsaturated compound with carbon monoxide and hydrogen, in the presence of said system and said solvent, the catalyst system obtainable by combining:
   a) a metal of Group VIII or a compound thereof; and
   b) a bidentate compound as defined in claim 2,
   and wherein the reaction medium is characterized in that a chlorine moiety is present in at least one of said Group VIII metal compound or said solvent, including the possibility of being present in both.

58. A process for the hydroformylation of ethylenically unsaturated compounds, said process comprising the step of reacting said ethylenically unsaturated compound with carbon monoxide and hydrogen, in the presence of a reaction medium as defined in claim 57.

59. The process of claim 55, wherein R represents a lower alkylene bridging group.

60. The process of claim 1, wherein R is a lower alkylene or A-Ar—B, in which Ar is an optionally substituted aryl moiety to which A and B are linked on available adjacent carbon atoms, and A and B each independently represent lower alkylene.

61. The process of claim 60, wherein the lower alkylene is selected from the group consisting of methylene and substituted variants thereof, ethylene and substituted variants thereof, propylene and substituted variants thereof, and butylene and substituted variants thereof.

\* \* \* \* \*